US010656254B2

(12) United States Patent
Nestler

(10) Patent No.: US 10,656,254 B2
(45) Date of Patent: May 19, 2020

(54) ANALOG ULTRASOUND BEAMFORMER

(71) Applicant: ANALOG DEVICES, INC., Norwood, MA (US)

(72) Inventor: Eric G. Nestler, Long Beach Township, NJ (US)

(73) Assignee: ANALOG DEVICES, INC., Norwood, MA (US)

( * ) Notice: Subject to any disclaimer, the term of this patent is extended or adjusted under 35 U.S.C. 154(b) by 617 days.

(21) Appl. No.: 15/352,760

(22) Filed: Nov. 16, 2016

(65) Prior Publication Data
US 2017/0146643 A1    May 25, 2017

Related U.S. Application Data

(60) Provisional application No. 62/257,706, filed on Nov. 19, 2015.

(51) Int. Cl.
*G01S 7/52* (2006.01)
*G10K 11/34* (2006.01)
(Continued)

(52) U.S. Cl.
CPC ........ *G01S 7/52047* (2013.01); *A61B 8/5215* (2013.01); *G01S 7/52003* (2013.01);
(Continued)

(58) Field of Classification Search
CPC ............. G01S 7/52047; G01S 7/52003; G01S 7/52095; G01S 15/8915; G01S 15/8927;
(Continued)

(56) References Cited

U.S. PATENT DOCUMENTS 4,550,607 A * 11/1985 Maslak ............... G01S 7/52046
73/626
5,784,336 A    7/1998 Gopinathan et al.
(Continued)

FOREIGN PATENT DOCUMENTS

CN    1189217 A    7/1998
CN    103076603    5/2013
(Continued)

OTHER PUBLICATIONS

Tai K. Song et al., *Ultrasonic Dynamic Focusing Using an Analog FIFO and Asynchronous Sampling*, IEEE Transactions on Ultrasonics, Ferroelectrics, and Frequency Control, vol. 41, No. 3, May 1994, 7 pages.
(Continued)

*Primary Examiner* — Krystine E Breier
(74) *Attorney, Agent, or Firm* — Patent Capital Group

(57) ABSTRACT

A sampled analog beamformer for ultrasound beamforming includes an array of transducers for transmitting analog signals and receiving reflected analog signals, and a sampled analog filter for filtering the received reflected analog. The sampled analog filter includes a delay line for adding a delay to each of the received reflected analog signals. Using a sampled analog filter in an ultrasound beamforming system reduces the power usage of the system and decreases the number of components in the system.

20 Claims, 17 Drawing Sheets

(51) Int. Cl.
   *G01S 15/89* (2006.01)
   *A61B 8/08* (2006.01)
   *A61B 8/06* (2006.01)
   *A61B 8/00* (2006.01)

(52) U.S. Cl.
   CPC ........ *G01S 15/8915* (2013.01); *G10K 11/346* (2013.01); *A61B 8/06* (2013.01); *A61B 8/4483* (2013.01); *A61B 8/5207* (2013.01); *G01S 7/52095* (2013.01); *G01S 15/8927* (2013.01); *G01S 15/8997* (2013.01)

(58) Field of Classification Search
   CPC ..... G01S 15/8997; A61B 8/06; A61B 8/4483; A61B 8/5215; G10K 11/346
   See application file for complete search history.

(56) References Cited

U.S. PATENT DOCUMENTS

| | | | |
|---|---|---|---|
| 6,248,073 | B1 | 6/2001 | Gilbert et al. |
| 6,673,016 | B1* | 1/2004 | Bolorforosh ............ B06B 1/064 600/437 |
| 7,250,885 | B1* | 7/2007 | Nairn .................. H03M 1/1215 341/141 |
| 7,993,270 | B2* | 8/2011 | Bae .................... G01S 7/52023 600/437 |
| 8,416,643 | B2* | 4/2013 | Magee ................. G10K 11/346 367/138 |
| 8,744,155 | B2* | 6/2014 | Walker ................ G01S 7/52046 382/131 |
| 8,834,369 | B2* | 9/2014 | Magee ................. G10K 11/346 367/103 |
| 9,091,749 | B2 | 7/2015 | Amemiya |
| 9,717,477 | B2* | 8/2017 | Hashiba ................ G01S 7/5202 |
| 9,739,875 | B2* | 8/2017 | Koptenko ............ G10K 11/341 |
| 9,767,818 | B1* | 9/2017 | Jain .................... G10L 21/0208 |
| 9,829,597 | B2* | 11/2017 | Zeroug .............. E21B 47/0005 |
| 9,960,827 | B2* | 5/2018 | Reinhardt ............ H04B 7/0691 |
| 10,107,645 | B2* | 10/2018 | Hajati ................... B06B 1/0207 |
| 10,269,096 | B2* | 4/2019 | Hancock ................ A61B 8/12 |
| 2002/0082500 | A1* | 6/2002 | Henderson .......... G01S 7/52095 600/443 |
| 2003/0069504 | A1* | 4/2003 | Wilkening ............. A61B 8/481 600/443 |
| 2004/0015079 | A1* | 1/2004 | Berger ................... A61B 8/546 600/437 |
| 2014/0249420 | A1* | 9/2014 | Akahane .................. A61B 8/54 600/459 |
| 2015/0151330 | A1* | 6/2015 | Tsuruno ................ B06B 1/0629 367/7 |
| 2016/0097846 | A1* | 4/2016 | Mortensen .......... G01S 7/52017 367/97 |
| 2017/0227630 | A1* | 8/2017 | Bagge ................. G01S 7/52025 |
| 2018/0003819 | A1* | 1/2018 | Koptenko ........... G01S 7/52025 |
| 2018/0017669 | A1* | 1/2018 | Lee ........................ A61B 8/145 |

FOREIGN PATENT DOCUMENTS

| | | |
|---|---|---|
| JP | 2007325937 | 12/2007 |
| JP | 10-179585 | 8/2010 |
| WO | 1997-01768 | 1/1997 |

OTHER PUBLICATIONS

Kai E. Thomenius, *Evolution of Ultrasound Beamformers*, 1996 IEEE Ultrasonics Symposium, © 1996 IEEE, 8 pages.

Lequan Zhang et al., *Design of a 64 Channel Analog Receive Beamformer for High Frequency Linear Arrays*, 2010 IEEE International Ultrasonics Symposium Proceedings, 4 pages.

Gokce Gurun et al., *An Analog Beamformer for Integrated High-Frequency Medical Ultrasound Imaging*, 978-1-4577-1470-2 © 2011 IEEE, 4 pages.

Ji-Yong Um et al., *A Single-Chip Time-Interleaved 32-Channel Analog Beamformer for Ultrasound Medical Imaging*, IEEE Asian Solid-State Circuits Conference, Nov. 12-14, 2012, Kobe, Japan, 4 pages.

A. Rothermel et al., *Analog Phase Measuring Circuit for Digital CMOS IC's*, IEEE Journal of Solid-State Circuits, vol. 28, No. 7, Jul. 1993, 4 pages.

Mostafa Fatemi et al., *Ultrasonic B-Scan Imaging: Theory of Image Formation and a Technique for Restoration1*, Ultrasonic Imaging and Tissue Characterization Symposium, Jan. 1, 1980, 48 pages.

Bruno Stefanelli et al., *An Analog Beam-Forming Circuit for Ultrasound Imaging Using Switched-Current Delay Lines*, IEEE Journal of Solid-State Circuits, vol. 35, No. 2, Feb. 2000, 10 pages.

English Google Translation of CN1189217A.

English Translation (Google) of the Bibliographic Data, Description and Claims for JP10-179585.

* cited by examiner

ANALOG ULTRASOUND BEAMFORMER

CROSS-REFERENCE TO RELATED APPLICATION

This application claims the benefit of priority under 35 U.S.C. § 120 of U.S. Application Ser. No. 62/257,706 filed Nov. 19, 2015, and entitled "Analog Ultrasound Beamformer", naming Eric G. Nestler as inventor. The disclosure of the prior application is considered part of and is incorporated by reference in the disclosure of this application.

FIELD OF THE DISCLOSURE

The present invention relates to the field of ultrasound technology, in particular to ultrasound beamformers.

BACKGROUND

Ultrasound uses echolocation for detection and imaging. Ultrasound machines utilize arrays of microphones and speakers to perform excitation and recording of echoes from the item being investigated. A signal including ultrasonic energy is transmitted through an ultrasound transducer in short bursts. After each burst, for a short period of time correlating to the amount of time for the ultrasonic energy to reach a target and reflect back to the transducer, the ultrasound machine receives reflected signals. Signals received during the short period undergo additional signal processing to determine the source locations of targets from which the signals reflected.

Traditional ultrasound systems have very high power requirements. One reason for the high power requirements is that these systems typically have 128 or more 12 or 14 bit analog-to-digital converters (ADCs) running at 40 Msps (mega samples per second) or more. In addition, in traditional systems, the beamformer is in the digital domain and consumes a great deal of power because it runs at the ADC sample rate for all 128 channels simultaneously.

SUMMARY OF THE DISCLOSURE

Systems and methods are disclosed herein for using sampled analog technology in an ultrasound system to reduce the power usage of the system and minimize the number of components in the system. In particular, the power usage is reduced to between about 2 and about 4 Watts. One way the system components are reduced is by decreasing the number of ADCs. The system components are reduced such that the components fit into the ultrasound probe.

According to one implementation, a sampled analog beamformer for ultrasound beamforming includes an array of transducers for transmitting analog signals and receiving reflected analog signals, and a sampled analog filter for filtering the received reflected analog signals and outputting sampled analog ultrasound signals. The sampled analog filter includes a delay line for adding a delay to each of the received reflected analog signals. The delay line adds a fractional delay and an integer delay to each of the received reflected analog signals.

In some implementations, the received reflected analog signals are pressure waves, and the array of transducers converts the received reflected analog signals to voltages. In other implementations, the received reflected analog signals are pressure waves, and the array of transducers converts the received reflected analog signals to currents.

According to some implementations, the sampled analog beamformer includes a farrow filter in the sampled analog filter for filtering the received reflected analog signals. In other implementations, the sampled analog beamformer includes a finite impulse response filter in the sampled analog filter for filtering the received reflected analog signals. In some implementations, the sampled analog beamformer includes an infinite impulse response filter (IIR) in the sampled analog filter for filtering the received reflected analog signals.

In some implementations, the sampled analog beamformer includes a fractional delay filter bank in the sampled analog filter for filtering the received reflected analog signals. In some examples, the fractional delay filter bank uses skewed sampling to select a subsample for transmitting with the filtered analog ultrasound signals. In some examples, the sampled analog beamformer includes a digital skew generator in the fractional delay filter bank for generating a time skew of delay between channels.

In some implementations, the sampled analog beamformer includes a summation module for summing the reflected sampled analog ultrasound signals and generating a beamformer output. In some implementations, the sampled analog beamformer includes an apodization circuit for windowing of a waveform of the transmitted sampled analog ultrasound signals to reduce sidelobes.

According to one implementation, a sampled analog beamformer for ultrasound beamforming includes a sampled analog filter for filtering an analog signal to form a sampled analog signal, and beamforming the sampled analog signal, and a summation node for adding the sampled analog signal to parallel sampled analog signals from parallel sampled analog beamformers.

In some implementations, a sampled analog beamformer includes a farrow filter in the sampled analog filter for introducing a fractional delay to the analog signal. In some implementations, a sampled analog beamformer includes a finite impulse response filter in the sampled analog filter for filtering the received reflected analog signals.

According to some implementations, a sampled analog beamformer includes a fractional delay filter bank in the sampled analog filter for filtering the analog signal to form the sampled analog signal. In some examples, the fractional delay filter bank uses skewed sampling to select a subsample for transmitting with the filtered analog ultrasound signals. In other examples, the fractional delay filter bank includes a digital skew generator for generating a time skew of delay between channels.

In some implementations, the sampled analog beamformer includes an apodization circuit for windowing of a waveform of the sampled analog signal to reduce sidelobes.

According to one implementation, a method for sampled analog beamforming includes transmitting analog signals from an array of transducers, receiving reflected analog signals at the array of transducers, filtering the received reflected analog signals with a sampled analog filter, and outputting a sampled analog signal from the sampled analog filter. Filtering includes adding a delay to each of the received analog signals. According to one example, the delay includes a fractional delay and an integer delay.

In some implementations, the method includes adding, at a summation node, the sampled analog signal to parallel sampled analog signals from parallel sampled analog beamformers. In some implementations, the method includes windowing, at an apodization circuit, a waveform of the sampled analog signal to reduce sidelobes.

According to various implementations, the analog beamformer can be used in any ultrasound, radar, and acoustics applications for low power beamforming. SAT can represent the building block for advanced ultrasound beamforming applications including synthetic aperture techniques, plane wave imaging, divergent beamforming, retrospective dynamic transmit focus applications, and subaperture array beamforming. SAT can be used in all beamforming applications including single-row (1D) ultrasound probes, and multi-row probes (1.5D, 1.75D, and 2D arrays), as well as catheter probes. SAT can be used in both probe and console (system) beamforming applications, including applications that require very low power, as well as high density applications. SAT beamforming can also be used in wearable ultrasound device form factors that incorporate beamforming. According to some implementations, SAT beamforming can be used for identity and security applications such as body part imaging. In some examples, SAT beamforming can be used for fingerprint imaging. In other examples, SAT beamforming can be used retinal imaging.

BRIEF DESCRIPTION OF THE DRAWINGS

To provide a more complete understanding of the present disclosure and features and advantages thereof, reference is made to the following description, taken in conjunction with the accompanying figures, wherein like reference numerals represent like parts, in which:

FIG. 4B shows a UABF system including multiple UABF blocks connected in parallel, according to one embodiment of the disclosure;

DETAILED DESCRIPTION

Figure 1:
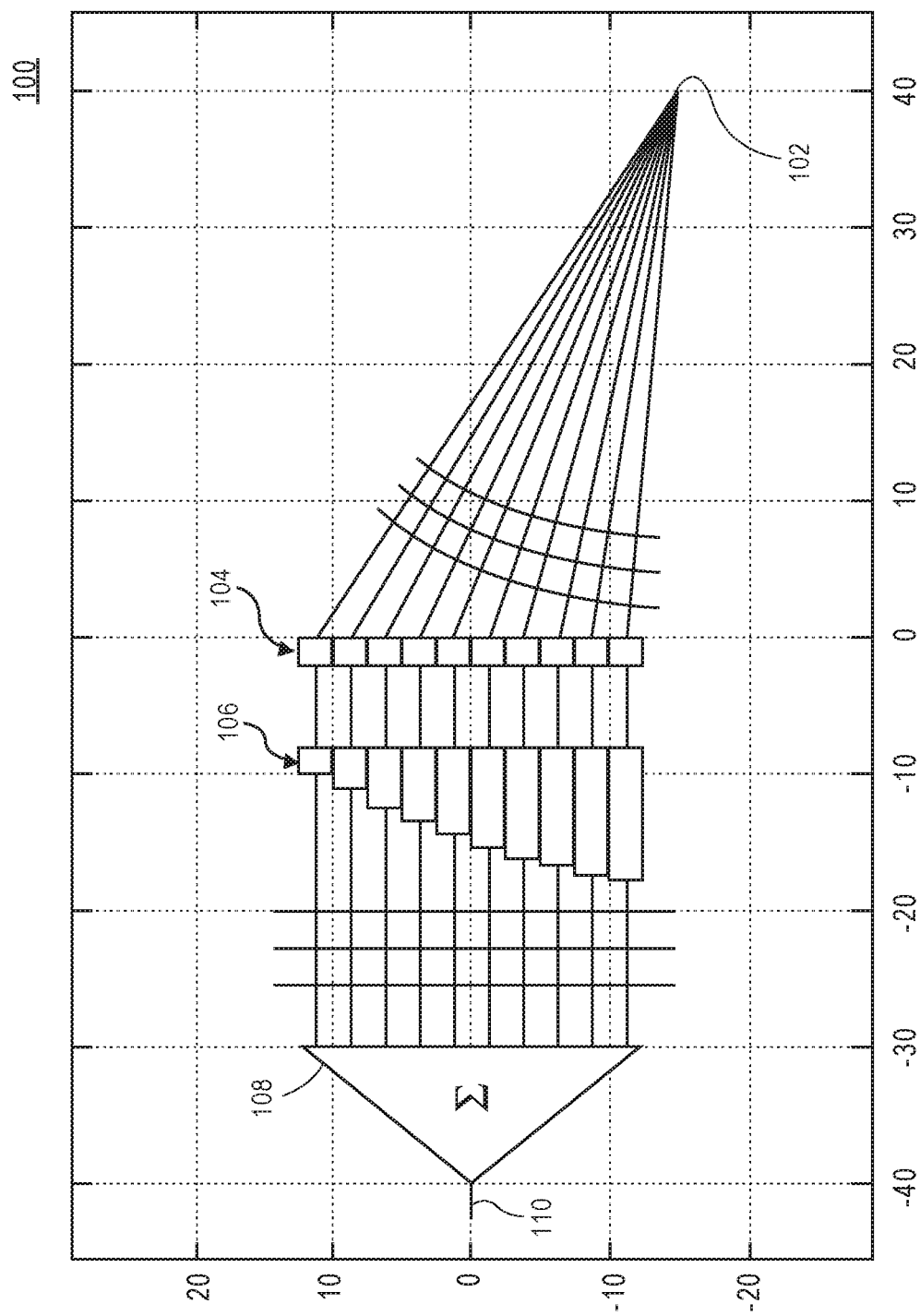
FIG. 1 is a diagram showing beam steering and focusing, according to some embodiments of the disclosure.

Systems and methods are disclosed herein for using sampled analog technology in an ultrasound beamformer. Sampled Analog Technology (SAT) refers to systems in which an incoming analog signal is used directly in the system without first being converted to a digital signal. Using sampled analog technology reduces the power usage of the beamformer and reduces the number of components in the system such that the ultrasound beamforming system fits into the ultrasound probe.

Ultrasound imaging products use delay-and-sum beamforming to focus transmit and receive pressure waves. Current ultrasound imaging products implement delay- and sum beamforming in the digital domain for performance reasons. However, Sampled Analog Technology (SAT) can perform delay-and-sum beamforming functions in the analog domain, thereby reducing the use of resources such as memory and power. Disclosed herein are systems and methods for a SAT Ultrasound Analog Beamformer (UABF) that uses more than one hundred times less power than traditional digital beamformers while maintaining image quality. The systems and methods for a UABF discussed herein enable a probe with the complete receive signal path electronics in the transducer probe itself, and provide high quality image data.

Sampled analog technology signal processing is performed in the analog domain by charge sharing among capacitors using only electronic switches and capacitor elements. A sampled analog filter filters incoming analog signals without first digitizing the signals. Sampled analog technology uses discrete time filter architectures combined with analog signal processing, which eliminates any data path quantization noise issues and analog-to-digital and digital-to-analog conversion steps.

Delay-And-Sum Beamforming

Delay-and-sum beamforming (BF) is a fundamental function for ultrasound imaging. It is a sampled data system in which the continuous time (CT) return signal is sampled after the transmit signal. The sample rate is related to power consumption, system performance, and image quality, such that reducing the sample rate reduces power consumption, and increases system performance. However, reducing the sample rate can decrease image quality. With a wideband transducer, which is used for harmonic imaging, the lowest sample rate that allows for accurate interpolation is four times the transducer center frequency ($f_c$). In one example, a 10 MHz transducer uses a 40 MHz sample rate. In other examples, a 10 MHz transducer uses sample rates that are greater than 40 MHz. At sample rates of 150 MHz and greater, the BF output has sufficient accuracy without interpolation.

The delay-and-sum output calculation is used for each channel of the transducer. In various examples, the transducer is a linear transducer and includes 32 channels, 64 channels, 128 channels, 256 channels, or more than 256 channels. In other examples, the transducer is a 2D transducer and includes 9,000 elements or more. The delay calculation includes an integer part (an integer number of samples at the sampling rate) and a fractional part. In some examples, at sampling rates of 150 MHz to 200 MHz, the fractional part of the delay calculation can be very small, and can be zero, but the integer part of the delay calculation becomes very large (800 to 1000 samples). The fractional delay part of the delay calculation is described in greater detail below.

For existing high quality medical imaging devices, the interpolation is done in the digital domain. The output of each transducer is converted to digital using 128 ADCs running at the sample rate. Nominally this is reduced to the four times the transducer center frequency to use present ADC technology with sufficient SNR. A digital delay-and-sum BF runs at 40 MHz on all transducer elements simultaneously. In the example case of a 128 element transducer there are 128 interpolators running simultaneously in real time. Interpolation is used for high quality images so that the fractional delay (FD) can be accurate over the entire bandwidth of the transducer. The fractional delay is typically 0.25 to 0.75 of Nyquist. In some examples, interpolation in the digital domain is done in an FPGA or custom ASIC. In current systems, the design uses a large amount of power and the system with the high power usage is too large to place in the probe handle with 128 ADCs. Interpolation systems and methods are described in greater detail below.

An analog BF solution as discussed herein can provide several major improvements. First, the power usage is reduced with a sampled analog technology (SAT) BF. Second, according to some implementations, only one ADC is used. There are many implementations of the SAT UABF as discussed herein, including variations, for example, in the transducer design, the ratio of $f_s$ to $f_c$, and the image quality. One detailed design discussed herein is for an 128 element transducer with a $f_s$ to $f_c$, ratio of $f_s=4*f_c$. The 128 element BF is entirely passive with 128 analog input waveforms and a single sampled analog output. One design implements a Farrow filter structure for the fractional delay component of the delay values, and an analog delay ring for the integer component of the delay values. The Farrow filter structure is designed using SAT. In other implementations, the design may include any selected number of transducer elements and other types of filter structures. In some implementations, the design includes multiple FIR filters, and in particular, includes a FIR filter for each fractional delay value. In some implementations, the design includes multiple FIR filters in series. In other implementations, the design includes multiple FIR filters in parallel. In further implementations, the design includes multiple FIR filters, with some FIR filters connected in series and others in parallel. In some implementations, the design includes polyphase filters.

FIG. 1 shows a simplified diagram of the signal path for a reflected wave front in a time domain delay-and-sum steering and focusing system. FIG. 1 also shows the delay profile used to focus and steer the received signal to a specific point. In one example, the array elements 104 in FIG. 1 are transducers. The transducers transmit a pressure wave and receive reflected pressure waves from a point source 102. The transducers each receive a pressure signal and convert it to an electronic signal. In one implementation, the transducers each receive a pressure signal and convert it to voltage. In another implementation, the transducers each receive a pressure signal and convert it to a current. The output of the transducers is sampled and the samples are filtered by the Farrow filters and delay lines 106. The outputs of the Farrow filters and delay lines 106 are summed at a summer 108 to result in the output 110.

According to various implementations, the UABF can perform at least two types of beamforming: sub-aperture beamforming and parallel receive beamforming. In sub-aperture beamforming, multiple BF blocks form beams for a sub-group of elements. In one example, for a 128 element transducer, there are 4 UABF blocks that each form beams for a 32 element sub-group of elements. The UABF blocks can form the beams contiguously, or the UABF blocks interleaved. In parallel receive beamforming, the UABF hardware is duplicated multiple times to create multiple simultaneous BF outputs, thereby increasing image update speed or frame rate. The frame rate is increased by the number of UABF blocks. In various examples, using two UABF blocks doubles the frame rate, using four UABF blocks increases the frame rate by a factor of four, and using eight UABF blocks increase frame rate by a factor of eight. In some implementations, the frame rate is increased by more than a factor of four, and every other output sample is used for the fractional delay. In one example, the frame rate is increased by a factor of eight, and every other output sample is used for the fractional delay output, such that the fractional delay output is at a four times frame rate. In some implementations, the alternative beamforming outputs use different delay profiles and operate as two times parallel beamformers.

In one implementation, the transducers are grouped into separate sections, which can each focus on different points. In one example, there are 128 transducers grouped into four separate transducer sections of 32 transducers each, and each section can focus on a different point. The signals received by the transducers in each section are filtered by Farrow filters and summed. When the transducers are grouped into multiple sections, the signals for each section of transducers are summed, resulting in one output per section.

UABF Circuit

Figure 2:
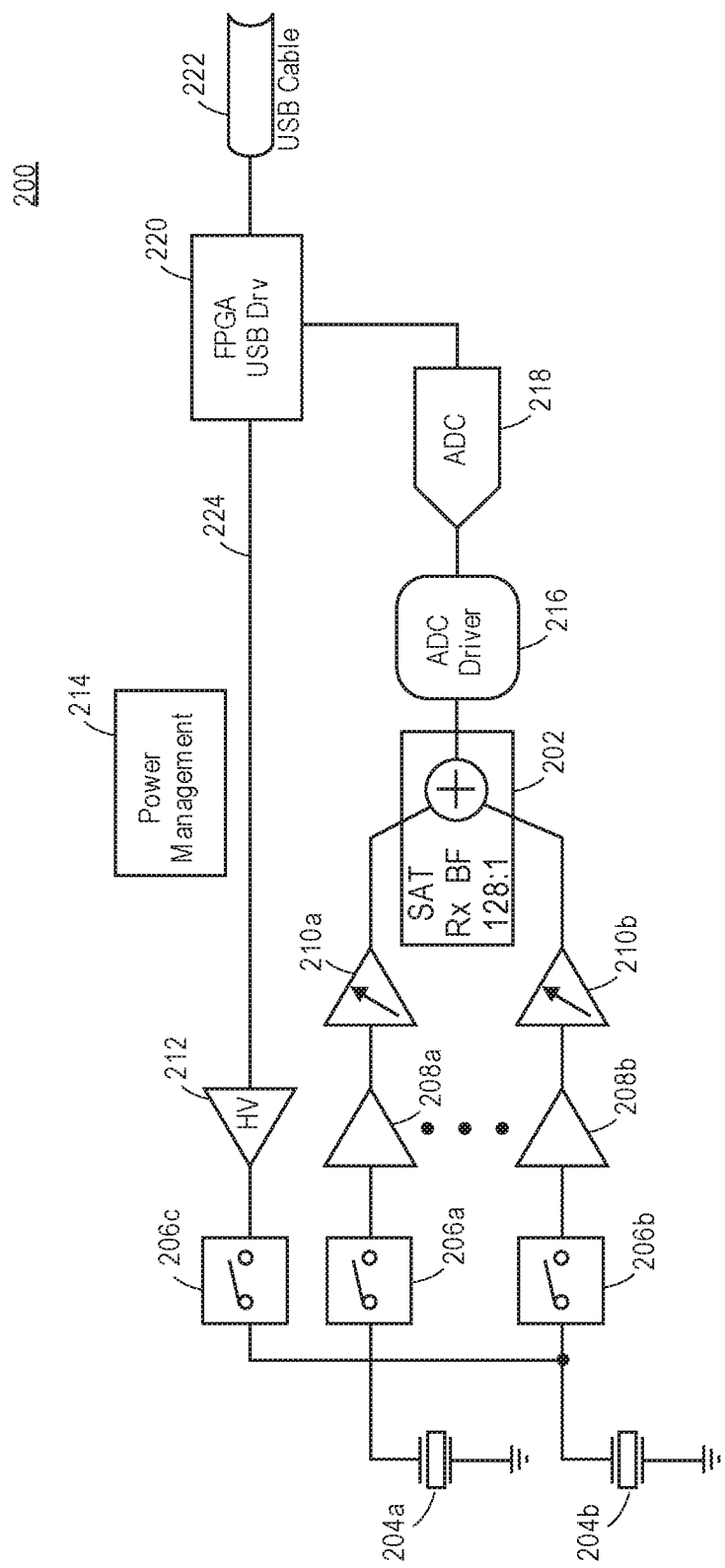
FIG. 2 illustrates an ultrasound analog beamformer (UABF) system, according to some embodiments of the disclosure.

FIG. 2 shows an ultrasound analog beamformer system 200 including a UABF circuit 202. The UABF system 200 includes multiple transducer elements 204a, 204b. When the UABF system is in receive mode, and is receiving reflected signals, the switch elements 206a, 206b are closed, and the reflected signals are received at the switch elements 206a, 206b. The output from the first 206a and second 206b elements is amplified at amplifiers 208a, 208b, and the outputs from the amplifiers 208a, 208b are processed at the variable gain amplifiers 210a, 210b.

The amplifier 208a is a low noise amplifier (LNA) and the amplifier 210a is a variable gain amplifier (VGA). In some implementations, there are 128 pairs of low noise amplifiers 208a and variable gain amplifiers 210a, one for each transducer. In some designs, the LNA and VGA are combined into one amplifier block. The LNA uses a low noise amplifier design to amplify the signal above the noise floor. In some examples, the VGA applies more gain as time increases, because the signal strength decreases as the target depth increases, due to loss in the body. In some examples, the VGA is referred to as time-gain-amplifier (TGA).

The output from the variable gain amplifiers 210a, 210b is input to the UABF block 202. In one example, the UABF block 202 includes two chips. In another example, the UABF block 202 includes one chip with two outputs. The output from the UABF block 202 is processed by an ADC driver 216, and then converted at an ADC 218. The output from the ADC 218 is input to a field programmable gate array (FPGA) USB driver 220, which sends the output from the ADC 218 to a console or computer to create the image. During receive mode, the third switch 206c is open.

In some implementations, a UABF system does not include an FPGA. In some examples, a UABF system includes a microprocessor or custom device instead of a FPGA. In other examples, a UABF system creates the image locally, and the locally created image is sent to a console or computer.

The UABF system 200 includes a transmit path 224. During transmit, the third switch 206c is closed, the FPGA 220 generates a waveform for transmission, and the waveform is input to a high voltage amplifier 212 (or puller) switches between drive voltages. The output from the high voltage amplifier 212 is transmitted through the third switch 206c to a transducer element 204b to generate a transmit pulse. In other examples, the output from the high voltage amplifier 212 is transmitted through the third switch 206c to a multiple transducer elements 204a, 204b. During transmit mode, the first 206a and second 206b switches are open.

The power management module 214 manages the power supplied to the UABF system 200. The transmit-receive sequence is repeated multiple times to make a single image. During transmit mode, the HV amplifier 212 is active for a short time (about a microsecond), and then the system 200 switches to receive mode. Receive control changes because initial echos are strong and subsequently weaken. The power management module 214 can control the voltage level of the HV amplifier 212, and the power of the input amplifiers 210a, 210b, to optimize power and to reduce power during periods when lower power levels are sufficient. In some examples, the power management module 214 can control the power of the input amplifiers 208a, 208b, to optimize power and to reduce power during periods when lower power levels are sufficient. In other examples, the power management module 214 can control the power of all amplifiers in the UABF system 200.

Figure 3:
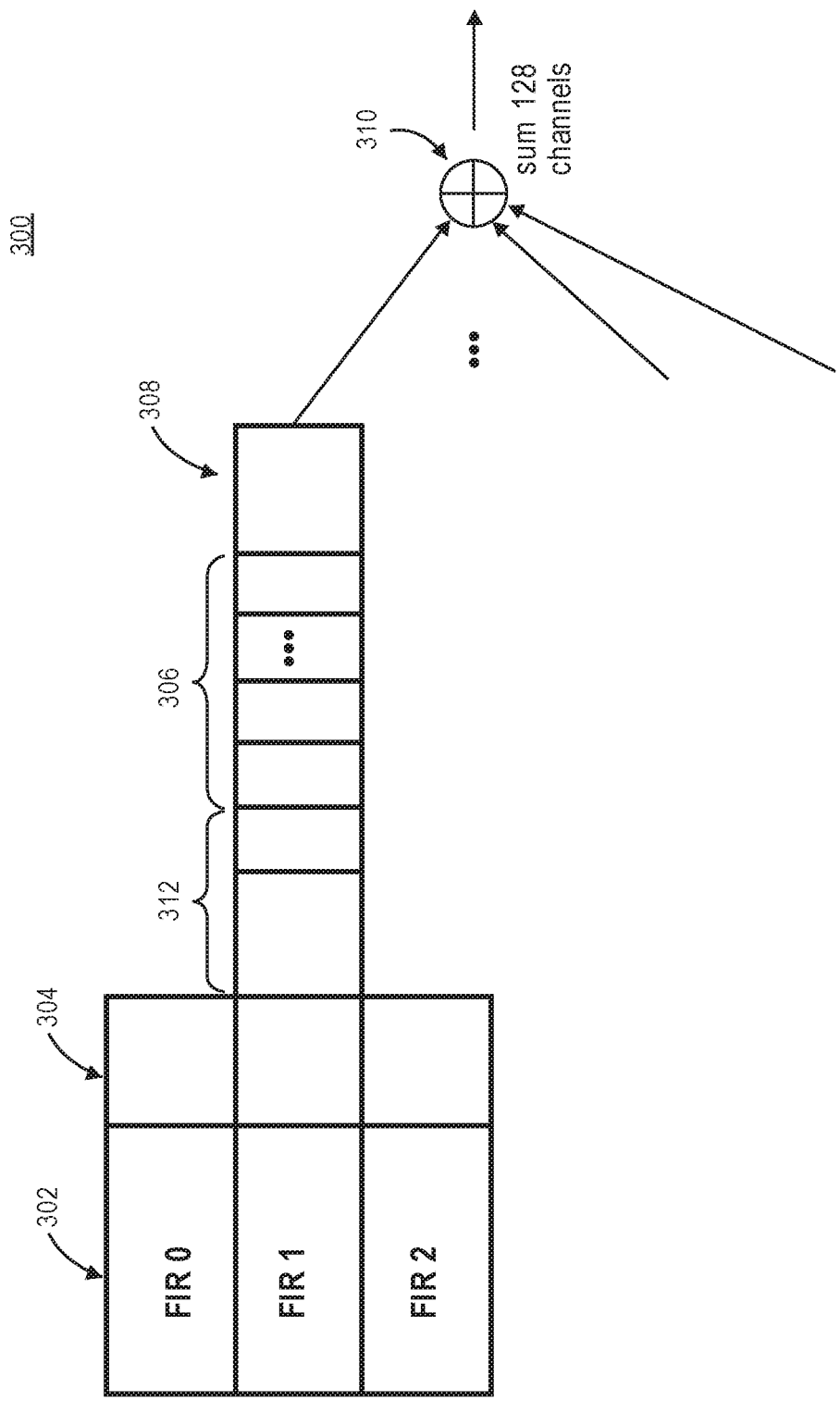
FIG. 3 is a block diagram showing the parts of a transducer section of an ultrasound analog beamformer, according to some embodiments of the disclosure.

FIG. 3 is a block diagram showing the parts of a SAT UABF block 300 of an ultrasound analog beamformer, according to some embodiments of the disclosure. The SAT UABF block 300 shows the elements for a single channel signal path through a UABF. In one example, the UABF block 300 is the UABF block 202 in FIG. 2. As shown in the UABF block 300, a UABF block 300 includes FIR filters 302, farrow scaling modules 304, integer delay lines 306, and an apodization section 308. In some implementations, a compensation capacitance module 312 may be included between the Farrow scaling modules 304 and the integer delay lines 306. The compensation capacitance module 312 may include one or more capacitors, and functions to adjust the total capacitance at the output such that it is constant for all delay values. The output from the section 300 is sent to a summer 310, where it is summed with outputs from other transducer sections. According to various implementations, as discussed in greater detail below, sampled analog technology can be used in the FIR filters 302 and in the Farrow filter scaling modules 304.

Figure 4A:
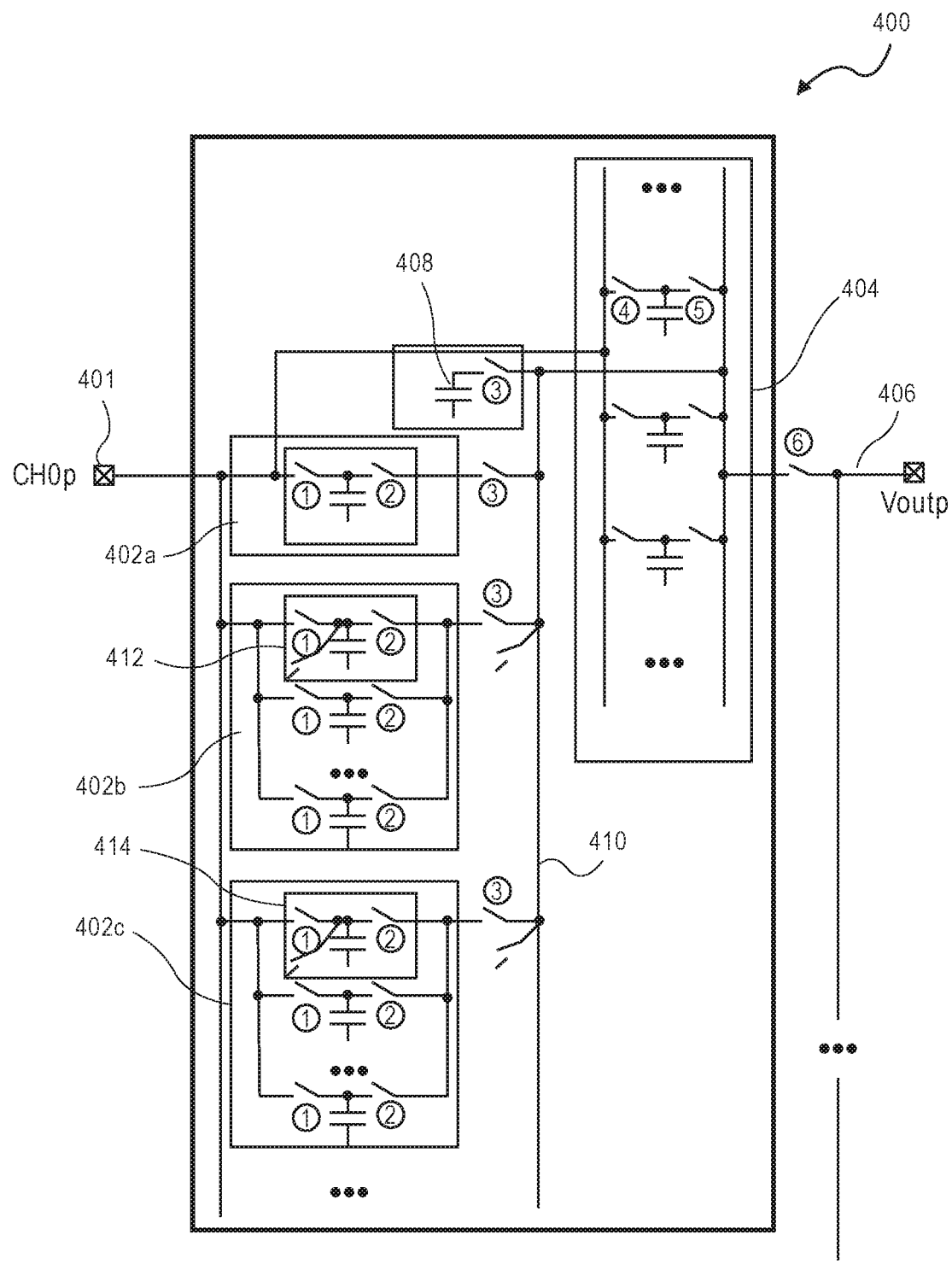
FIG. 4A shows Farrow filter design channel detail, according to some embodiments of the disclosure.

FIG. 4A shows a UABF block 400 including a Farrow filter and delay line circuit, according to some embodiments of the disclosure. The UABF block 400 includes three FIR sections 402a, 402b, and 402c, integer delay line 404, a compensation capacitor 408, and an output 406. The output 406 from the Farrow filter and delay line module 400 is Voutp. An implementation with multiple sections of transducers includes an output Voutp for each section. As shown in FIG. 4A, the UABF block 400 is a single passive multi-step charge sharing signal path. In one example, multiple UABF blocks 400 are used on one die to form a complete multi-element analog beamformer. For example, 128 UABF blocks 400 can be used on one die to form a complete 128 element analog beamformer. In some implementations, the UABF block is fully differential, and includes an output Voutn and an output Voutp. In other implementations, the UABF block is implemented as a single-ended circuit.

The UABF block 400 includes three FIR sections 402a, 402b, and 402c, which sample the input waveform 401. The three FIR sections 402a, 402b, and 402c are connected to form the Farrow output 410. The first FIR section 402a has a single unit capacitor in the center. The second 402b and third 402c FIR sections each include an FIR leaf cell 412, 414 respectively, and multiple capacitors. According to one example, the FIR output for the second 402b and third 402c FIR sections is formed when all of the capacitors are connected together.

The output from the FIR filters 402a, 402b, and 402c form the Farrow output 410, which is input to the to the integer delay line 404, along with the output from the compensation capacitor 408. The integer delay line 404 adds the integer delay to the Farrow output 410, and outputs the channel-delayed output Voutp 406. The compensation capacitor 408 functions to adjust the total capacitance at the output such that it is constant for all delay values. In some examples, the UABF block 400 does not include a compensation capacitor 408.

According to some implementations, the FIR sections 402a, 402b, and 402c are SAT FIR filters. In one example, the second 402b and third 402c FIR sections are each an M×M array of tiles, and are implemented as streaming FIR filters. Systems and methods for implementing the FIR sections and the Farrow filter as an SAT switchcap circuit structure are described in greater detail below and with reference to FIGS. 8, 9, and 10A-10C.

According to other implementations, a UABF block such as UABF block 400 includes one or more additional FIR sections 402a, 402b, 402c. For example, a UABF block may include about two, about four, about six, about eight, about ten, or more than ten FIR sections. In some implementations, a UABF block such as UABF block 400 includes fewer FIR sections 402a, 402b, 402c. For example, a UABF block may have one, two, three, or four FIR sections. In some implementations, the first FIR section 402a includes a FIR leaf cell and multiple capacitors, similar to the second 402b and third 402c filter sections.

Figure 4B:
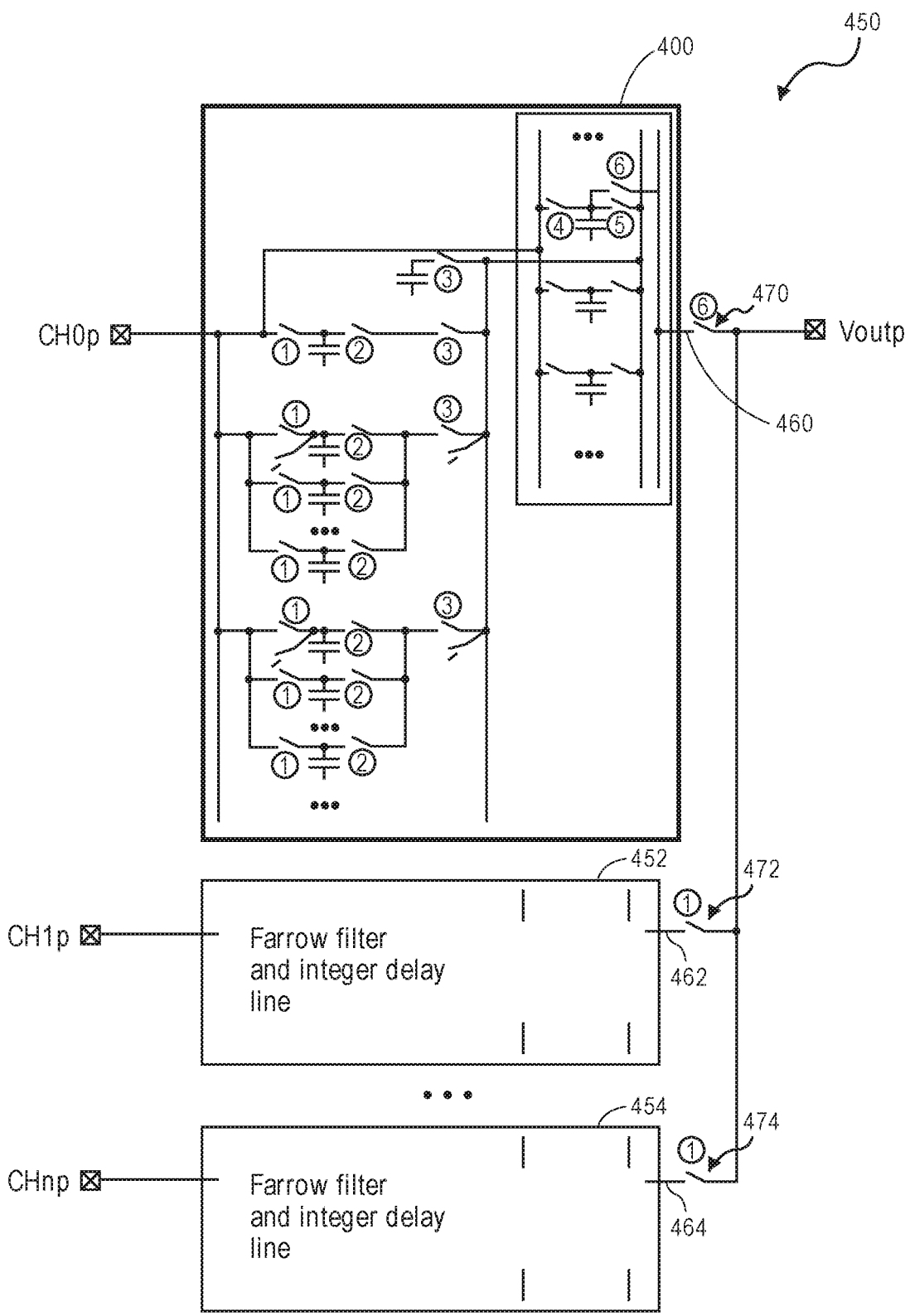
FIG. 4B shows

FIG. 4B shows a UABF system 450 including multiple UABF blocks connected in parallel, according to one embodiment of the disclosure. The UABF system 450 including a first UABF block 400, as described above with respect to FIG. 4A, as well as second 452 and third 454 UABF blocks. The first 460, second 462, and third 464 outputs from the respective UABF blocks 400, 452, and 454 are connected in parallel, and there is a switch 470, 472, 474 between each UABF block output 460, 462, 464 and the UABF system output 406. Thus, the UABF system output can include one or more UABF system 400, 452, 454 outputs combined.

In some examples, the UABF includes 128 transducers. In other examples, there are 16 transducers, 32 transducers, 64 transducers, 256 transducers or other numbers of transducers.

In some implementations, the outputs of the transducers are sampled at 40 MHz, yielding outputs every 25 nanoseconds. The outputs are sampled for a period of time equal to at least twice the transit time for the pressure waveform focusing on a target point the furthest distance away. The further the distance a transducer is focusing on, the longer the pressure waveform takes to reach the target point (transit time). After reaching the target point, the pressure waveform is reflected back to the transducer. The time for the reflected pressure waveform to return to the transducer is the same as the time as the pressure waveform took to reach the target point from the transducer (the transit time). After the outputs from the transducers have been sampled for a period of time equal to at least twice the transit time, the sampling is repeated for a next transmit pulse and receive time cycle. In various examples, the sampling is repeated about one hundred times or more than one hundred times to gather the data to form an image. In this manner, an image is formed for display.

In some implementations, fast image frame rates allow for extraction of transient image information such as blood flow, heart rates, umbilical cord flow, and other biomedical information. To yield fast image frame rates, multiple beamforming structures are used, requiring vast amounts of hardware and power. For example, 128 parallel beamforming structures such as the structure illustrated in FIG. 1, each with 128 transducers, can be used to yield high frame rates. In some examples, by multiplying the hardware used, imaging can show several thousand frames per second. According to some implementations, parallel beamforming can be implemented using the UABF disclosed herein without the vast hardware, memory, and power requirements of traditional beamformers.

In some examples, sub-aperture and parallel beamforming can be used together for efficient high resolution ultrasound beamforming.

According to various implementations, the delay calculation for a fractional delay value uses an interpolator to get accurate results over a wide bandwidth. In practice there are two components to the delay values used for steering and focusing. The total delay can be on the order of 100 microseconds in time and this time delay will be many samples at a selected sample rate ($f_s$). The result is that a specific delay value has both an integer value and a fractional value. The integer component can be exact and the fractional component calculation can have errors over frequency. Various implementations of the fractional delay (FD) part of the delay profiles to reduce errors over frequency are discussed herein.

In an idealized wide bandwidth transducer, the frequency bandwidth of the transducer element encompasses frequencies around the transmit frequency $f_o$ and the receive frequency $2f_o$. Thus, a transducer used for harmonic imaging has a wide frequency bandwidth. The fractional delay is calculated over the wide frequency range including both the transmit and receive frequencies, including the received pressure waveform which includes both the fundamental and all of the harmonics. Thus, the upper frequency limit of the wide bandwidth of the transducer is within the range of the accuracy of the interpolator.

According to one implementation, the design for the sampling of the transducer output is four times the center frequency ($f_c$). The transducer center frequency is then at 0.5 of Nyquist (0.25 of $f_s$). For a 100% transducer (the bandwidth of the transducer goes from $f_c$−50% to $f_c$+50%, and thus the difference is 100% or equal to $f_c$) the maximum frequency is 0.5+50%=0.75 fraction of Nyquist, and the minimum frequency is 0.5−50%=0.25 fraction of Nyquist. According to other implementations, other transducer designs with different bandwidths are used. In one example, a transducer with more than 100% bandwidth is used, and in one example, the UABF is operated at $f_s=5*f_c$.

According to another implementation, the FD accuracy is better than $1/(16*f_s)$. Thus, if the sample rate is 16 times the sampling frequency, then using the nearest sample method will be accurate. Similarly, if the sample rate is 8 times the sampling frequency, then interpolation to half a sample period will result in the 16 times frequency in time delay. In another example, the fractional delay is +0.25, and the accuracy is about 0.25.

In some examples, the range of accuracy for FD resolution varies by an amount that is half way between the current FD value and the next FD value. In one example, the FD resolution is ⅛ of $f_s$ for $f_s=4*f_c$, the next FD values are 0.25 and 0.375, and the range of accuracy is from 0.25−0.0625 to 0.25+0.0625 (half way between 0.25 and 0.375 is 0.3125, which is 0.0625 above 0.25 reference). 0.0625 is 1/16 of $f_s$ or 1/64 of $f_c$ ($f_c=4*f_s$).

For a sample rate at four times the transducer center frequency, the minimum delay accuracy is ¼ a sample period. However, systems and methods are provided for the delay accuracy to be ⅛ the sample period and allow the delay over frequency to have some error band. See the section "Interpolation" for more discussion about the oversampling ratio (fs/fc).

Laboratory measurements of commercial wide bandwidth transducers and narrow bandwidth transducers show that gain varies over frequency. In one example, a wide bandwidth transducer has a ~−5 dB droop of gain over the bandwidth. For harmonic imaging, the bandwidth around 10 MHz is approximately +−2.5 MHz. For both wide bandwidth and narrow bandwidth transducers, the band from 7.5 MHz to 12.5 MHz has a loss of amplitude of ~−2 dB or −3 dB compared to the center frequency 10 Mhz. This is about a 25% gain loss (−2 dB).

Additionally, in previous transducer systems, filters used different filter tap weights for each delay value. In some implementations, SAT FIR filters use different filter tap weights for each delay value. However, changing the delay at every sample time and for every transducer element uses a large amount of memory and high memory access rates. Additionally, changing the delay at every sample time and for every transducer element results a large number of delay values, which takes up a large area in the system and consumes more power than having a small number of delay values. Systems and methods are provided herein for a fractional delay filter with a gain error that is +−10% or +−0.8 dB compared to the center frequency, reduced power consumption and reduced memory access rates, and using smaller amounts of memory as compared to traditional ultrasound transducers.

Fractional Delay

A fractional delay electronic device is used to create interpolated values between consecutive sample times. The ideal fractional delay (FD) element is an infinite sequence when the delay value is not an integer number of samples. However, an ideal FD with an infinite sequence is non-causal and non-realizable. For example, in a filter for an integer delay of three samples, all the impulse response amplitude values at the sampling times are zero, except for a single unity value in the center, at the 3 sample index. However, when the delay is a fraction of a sample time, the non-zero sequence of amplitude values at the sampling times is infinitely long. However, the infinitely long non-zero sequence of amplitude values at the sampling times is non-casual and non-realizable. Systems and methods are provided herein to make an accurate approximation of the ideal filter that is causal and realizable.

Many different approaches have been used to make an ideal fractional delay (FD) element realizable with approximations, including windowing, least-squares error minimization, and Lagrange interpolation. However, the net result for discrete time systems is a fundamental limit of the bandwidth relative to the Nyquist frequency, where the fractional delay and filter magnitude are flat within some error limit. The Lagrange interpolation method can be used to illustrate this behavior. In particular, for a third order maximally flat FD filter, the magnitude of the normalized frequency is close to zero decibels (dB) from zero to about 0.2 of the Nyquist frequency. Similarly, the phase delay in samples is close to ideal for each fractional delay up to about 0.2 of the Nyquist frequency. One conclusion is that, unless the signal is bandlimited to less than 0.2 of Nyquist, to extend the flat region beyond 0.2 of Nyquist requires a higher order interpolator.

Lagrange Interpolation can be used for FIR and IIR approximations, and the results of the interpolation compared to the ideal delay element. Using Lagrange interpolation for FIR and IIR approximations results in magnitude errors versus frequency, and there is a bandlimited error for a fractional delay. In some examples, the bandlimited error can be up to 0.8 of Nyquist. Lagrange is another type of filter, and can provide very accurate approximations with a higher order design.

Interpolation

As discussed above, interpolation is used for high quality images so that the fractional delay (FD) can be accurate over the entire bandwidth of the transducer. While interpolators and FD filters and can be used in many types of product, they have some unique properties when used in ultrasound imaging.

The delay-and-sum beamforming includes interpolation of sampled values when the sample rate is lower than the delay quantization. The implementation complexity for interpolation is a continuum. At fast sampling rates ($f_s=16*f_c$, where $f_c$ is the transducer center frequency), delay-and-sum beamforming can be done without interpolation. The 16 times ratio ($f_s/f_c$) is a rule of thumb value for medical ultrasound imaging delay accuracy in units of time. A digital ultrasound beamformer using a sampling rate equal to 16 times the transducer center frequency (or greater), includes an ADC running at the sampling rate.

As $f_s$ is reduced, however, the delay accuracy can be met using interpolation. In order to get an accurate estimate of a sub-sample time value, the waveform shape is taken into account, which is the function of higher order interpolation methods.

Two types of interpolation include linear interpolation and cubic spline interpolation. When the use of linear interpolation is compared to the use of cubic interpolation on a sinewave curve, the error of the interpolated values near the sinewave peak is much smaller for the cubic spline interpolation value than the linear interpolation value. In general, higher order interpolation methods reduce the error of the interpolated values near the sinewave peak, and other higher order interpolation methods can be used to reduce error. The FD filter of the beamformer controls for the error in the interpolated value. In addition, the FD filter minimizes the error for a range of frequencies, where the range of frequencies is determined by the sample rate and the transducer center frequency.

As $f_s$ is increased, the fractional delay increments for controlling the error are reduced from $\frac{1}{8}*f_s$ to $\frac{1}{4}*f_s$ and then $\frac{1}{2}*f_s$. For each of these delay increments the allowed error can also increase. This allows the FD filter design constraints to be relaxed as the delay increments are increased (⅛ to ¼ to ½). Thus, increasing the delay increments reduces the area of the filter. There are several considerations to increasing the delay increments, including:

(1) The power to generate the digital strobes for the FD filter increases as the sample rate increases. The relationship between the total number of taps and the delay increment is not linear. The total number of taps determines the digital strobe design and its power consumption.

(2) The ADC sample rate does not increase. Thus, the input sampling of the SAT interpolator increases, but the interpolator output rate is still $4*f_c$. Additionally, the integer delay definition remains the same.

(3) When $f_s$ is increased such that no interpolation is needed, no FD filter is needed and the interpolator output only selects the correct nearest sample. This is described in greater detail below in the section titled "Skewed Sampling".

There is a continuum for the $f_s/f_c$ ratio of the FD filter design parameters and the maximum length of the integer delay. The continuum can be used to optimize various properties of the entire BF block.

Skewed Sampling

Figure 5:
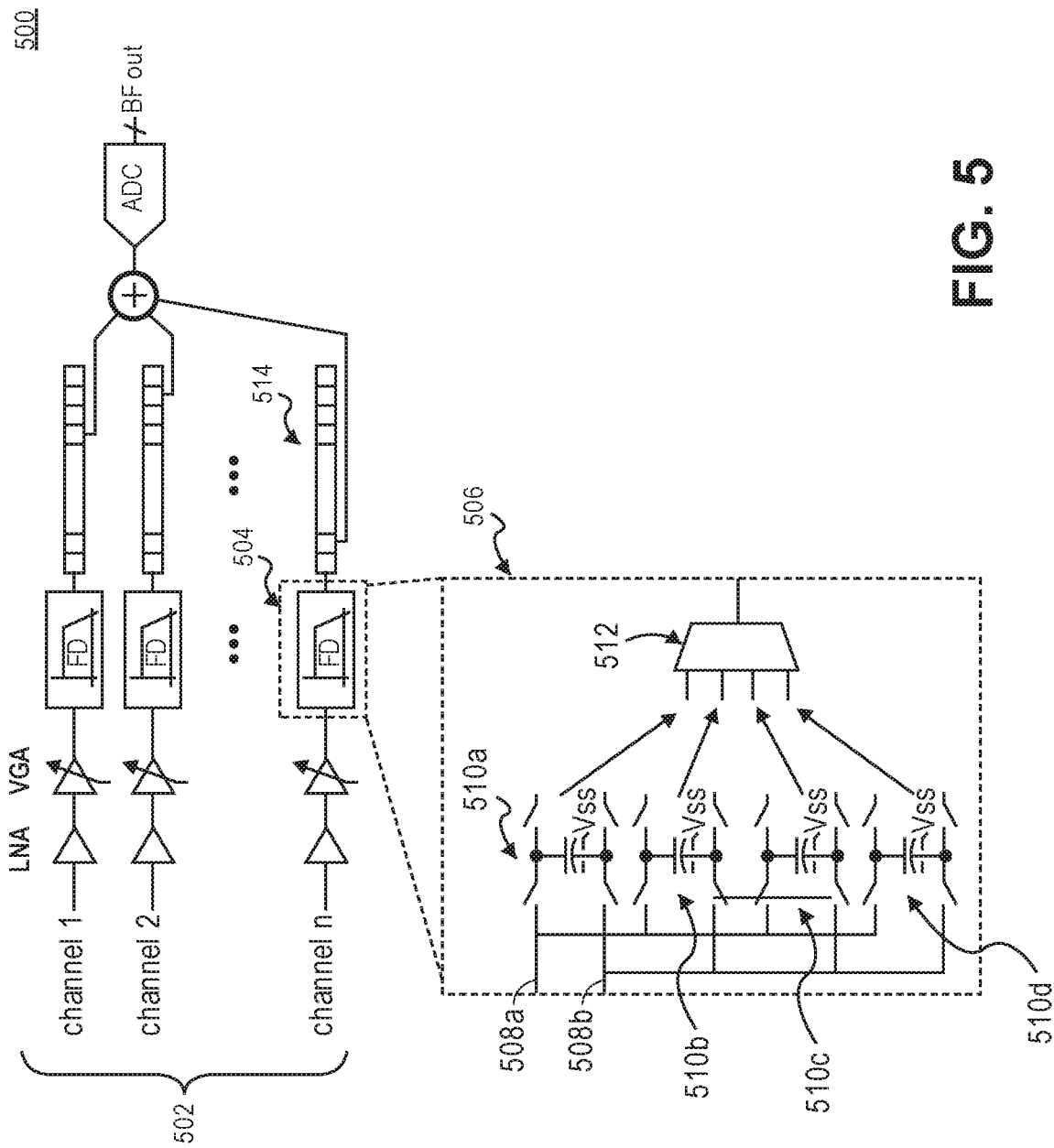
FIG. 5 shows a skewed sampling diagram, according to some embodiments of the disclosure.

As discussed above, when the $f_s/f_c$ ratio is increased to a selected rate (e.g., $f_s=16*f_c$) or higher, no interpolation between samples is needed. In this case, the interpolator selects which sample of the output sample rate to use for the fractional delay component of the delay profile. A diagram 500 showing an implementation of skewed sampling is shown in FIG. 5. FIG. 5 shows multiple input channel lines 502. A fractional delay filter 504 from one of the input channel lines is magnified in block 506 to show more detail.

As shown in block 506, the input to the fractional delay filter 504 is a differential input having two input terminals 508a, 508b. The input sample rate is four times the output rate, and, as shown inside the block 506, there are four switched capacitor circuit elements 510a-510d, and each switched capacitor circuit element 510a-510d samples the differential input components 508s, 508b and outputs a sub-sample. An interpolator 512 receives the four sub-samples and selects which of the four sub-samples to use as the input to the integer delay line 514. According to one implementation, the channels 502 are substantially the same and the sub-sampling capacitors 510a-510d are sampled substantially simultaneously for all channels. This property reduces error at the interpolation block 512. In other implementations, the circuit shown in FIG. 5 is a single-ended circuit.

Figure 6:
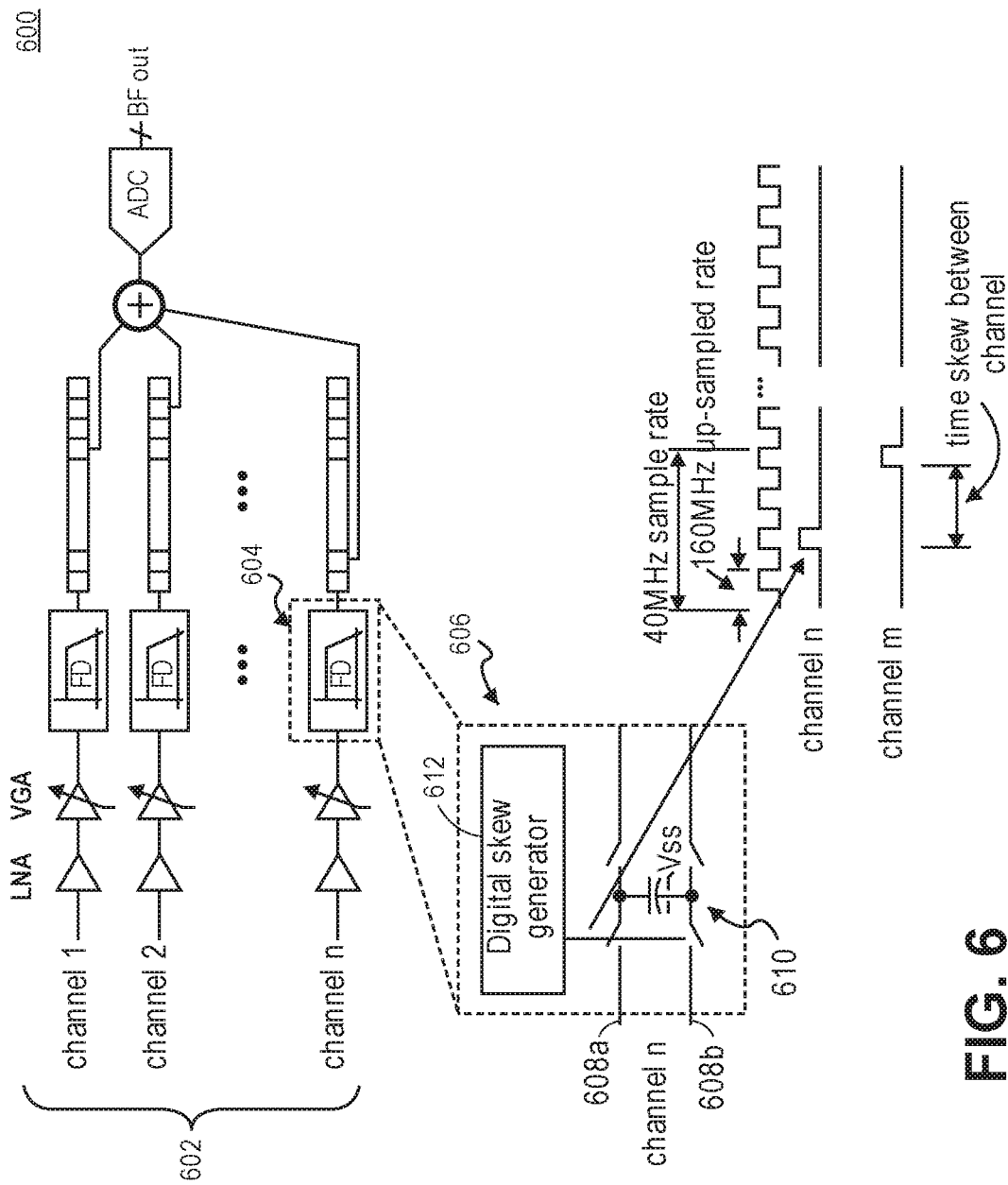
FIG. 6 shows digital skewed sampling, according to some embodiments of the disclosure.

Another implementation for skewed sampling is shown in the diagram 600 in FIG. 6. FIG. 6 shows input channels 602, and includes a block 606 that shows a magnified view of a fractional delay filter 604. As shown in block 606, the fractional delay filter 604 receives input components 608a, 608b, and includes a switched capacitor 610 and a digital skew generator 612. The digital skew generator 612 moves the sub-sampling and nearest sample selection into a digital block. The digital skew generator 612 generates the time skew of the delay between channels using a high frequency clock input. The time skew of delay between input channels 602 makes up the delay profile.

According to some implementations, using the system shown in FIG. 6, the input samples for each channel are not simultaneously sampled, which adds complication to generating the time skew of delay between channels. In particular, each channel has its own sampling strobe that is moved within the output sample rate ($f_s/f_c$ ratio) and these strobes are generated with different digital delays inside the digital block. The digital delays vary considerably over process, voltage and temperature. Additionally, the power usage of the digital block increases with the increased complexity of the design.

Figure 7:
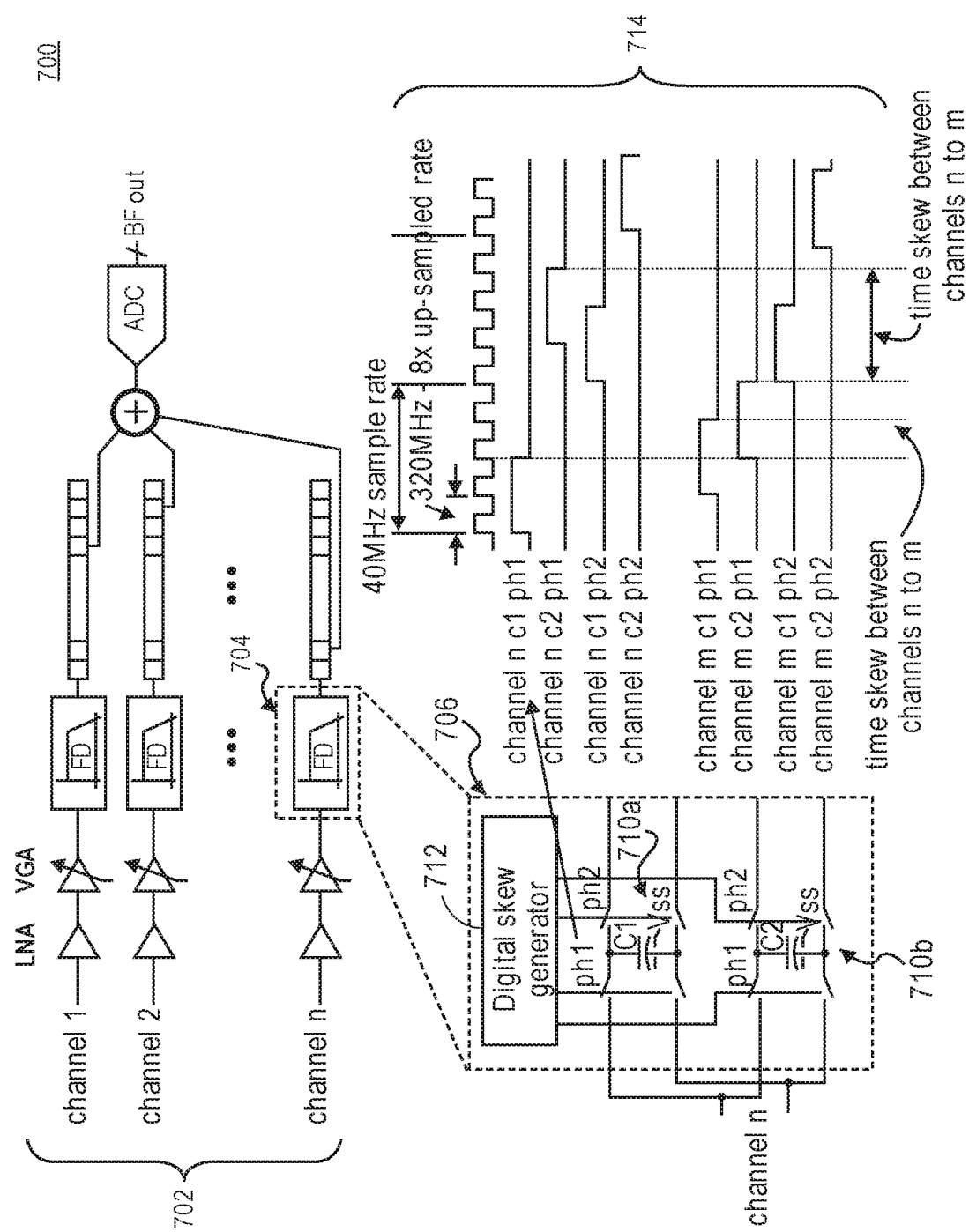
FIG. 7 shows a skewed sampling system including multiple sampling capacitors, according to various embodiments of the disclosure.

FIG. 7 shows another system 700 for skewed sampling including multiple sampling capacitors 710a, 710b, according to various embodiments of the disclosure. Each capacitor has a sample period (or window). The voltage on the capacitor settles to some accuracy. As shown in FIG. 7, the sampling strobes (ph1s) overlap with each other. In one example, including multiple sampling capacitors 710a, 710b allows timing the settling such that the UABF driver has a similar time period for settling as in the implementations shown in FIGS. 5 and 6. In one example, including multiple sampling capacitors 710a, 710b allows substantially simultaneous settling.

The system shown in FIG. 7 allows more time for settling than the systems in FIGS. 5 and 6. In one example, the settling time for the system 700 of FIG. 7 is $1/f_s$ with $f_s=4*f_c$, and the settling times for the systems of FIGS. 5 and 6 are $1/f_s$, but much shorter since $f_s=16*f_c$.

FIG. 7 shows a timing diagram 714. The sampling capacitors 710a, 710b allow delaying the charge reading operation (ph2 timing) so that the charge readout can be delayed to a later sample period. This allows the sampling and readout time period to be ½ of the 40 MHz period. In one example, the ph2 strobes select which capacitor sample is used for the FD value.

As shown in the system 700, there is no charge sharing or charge scaling, and the signal path gain is one for this circuit. Additionally, the analog core area for the Fractional delay filter 704 is much smaller than the Farrow filter design shown in FIG. 3 since there are only two capacitors per channel. Thus, total area is smaller. However, the digital skew generator 712 increases the power consumption of the system 700 as compared to the filter design shown in FIG. 3.

According to various implementations, the fractional delay filter 704 is coupled to an integer delay line. The integer delay line is one of a digital integer delay line and an analog integer delay line. According to some implementations, the fractional uses digital timing, and thus the sampling capacitors of the 128 channels are not sampled simultaneously, which can result in cross-coupling at sampling times between channels. According to some examples, careful circuit layout can prevent cross-coupling.

According to some implementations, a UABF with a fractional delay filter uses more power than a UABF with a Farrow filter because it uses higher clock frequencies. In one implementation, the fractional delay is completed in the digital domain at 32 times the center frequency, resulting in a clock frequency of 320 MHz. In one example, a system using a 320 MHz clock frequency consumes about ten times more power than the strobe generator used with a Farrow structure as described herein. Additionally, the 320 MHz clock period represents the fractional delay resolution. To ensure that the delay is accurate over the operation and frequency, there are separate strobes for each capacitor set in each channel, for the 128 channels. The skew between these digitally generated strobes is an analog specification.

Thus, skewed sampling uses more power than a Farrow structure, but is a much smaller structure.

Figure 8:
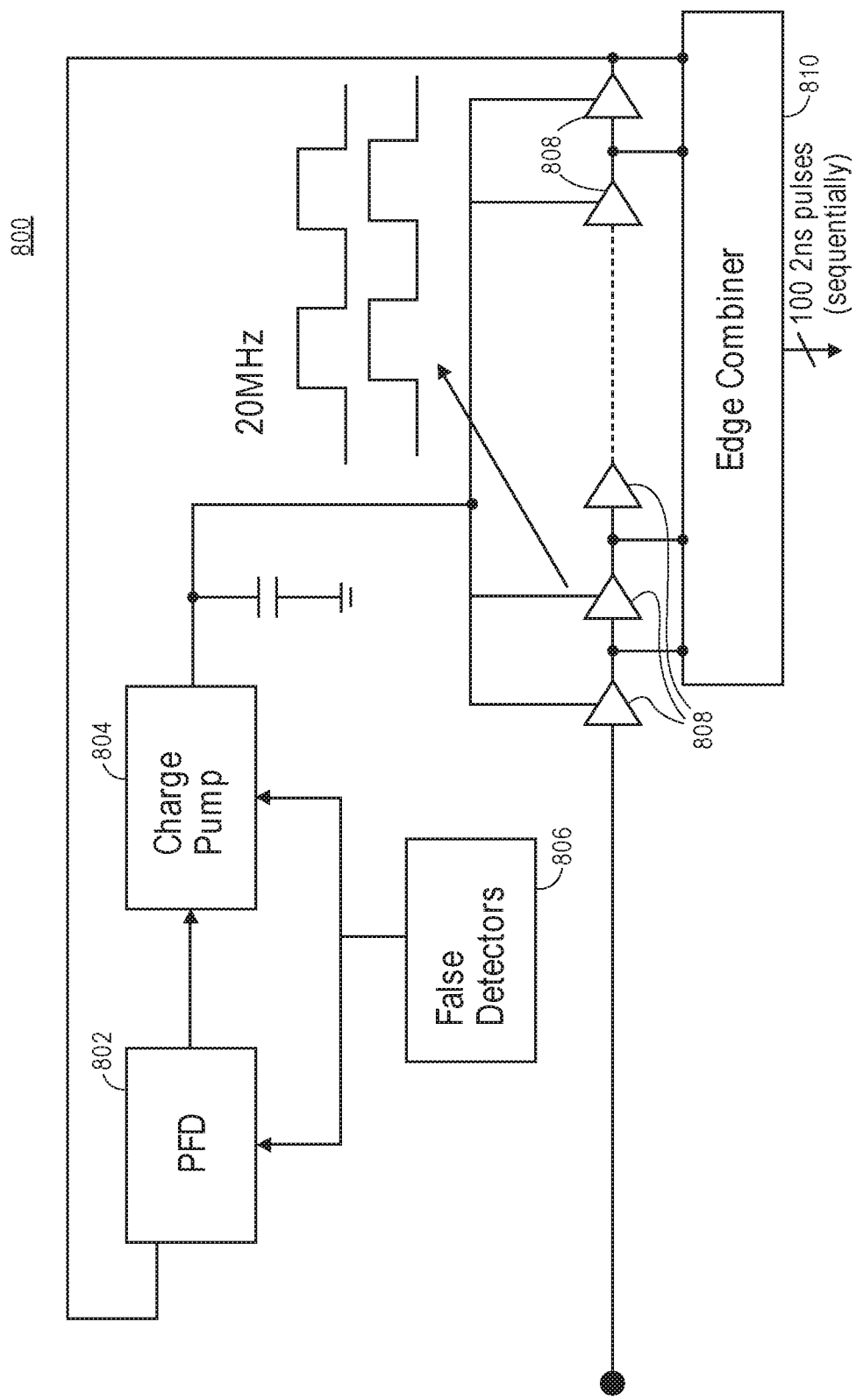
FIG. 8 shows a clock skew generator, according to some embodiments of the disclosure.

FIG. 8 shows a clock skew generator 800, according to some embodiments of the disclosure. The clock skew generator 800 can be used to generate sampling strobes, such as the sampling strobes (ph1's) in FIG. 7. The clock skew generator 800 includes a phase frequency detector (PFD) 802, an analog charge pump 804, a false detectors block 806, amplifiers 808, and an edge combiner 810. The PFD 802 has two input signals and compares the phase of the two input signals. The clock skew generator 800 includes a control loop that varies the analog charge pump 804 output frequency such that the output frequency is n times the sample rate. The false detectors block 806 prevents startup errors, glitch errors, and prevents the analog charge pump 804 from locking onto fake output frequencies (frequencies other than n times the sample rate). According to one implementation, for a UABF system, the clock skew generator 800 uses a 40 MHz clock input and the edges are skewed by 25 ns/8=3.12 ns using an eight tap delay chain. The edge combiner in the UABF system generates the longer sampling and ph2 strobes shown in FIG. 7.

According to one implementation, one clock skew generator 800 drives the 128 channels of a UABF transducer. The skew generator 800 is a larger size than other skew generator designs, and includes more digital gates. In one example, a low power process node is about 40 nm, and includes a skew generator. Additionally, the skew generator 800 has a larger capacitor density, and thus more femtoFarads per unit area. In one example, the clock skew generator 800 is a LIDAR clock skew generator. LIDAR is a form of radar using laser light instead of radiofrequency microwave signals.

Farrow Architecture

Figure 9:
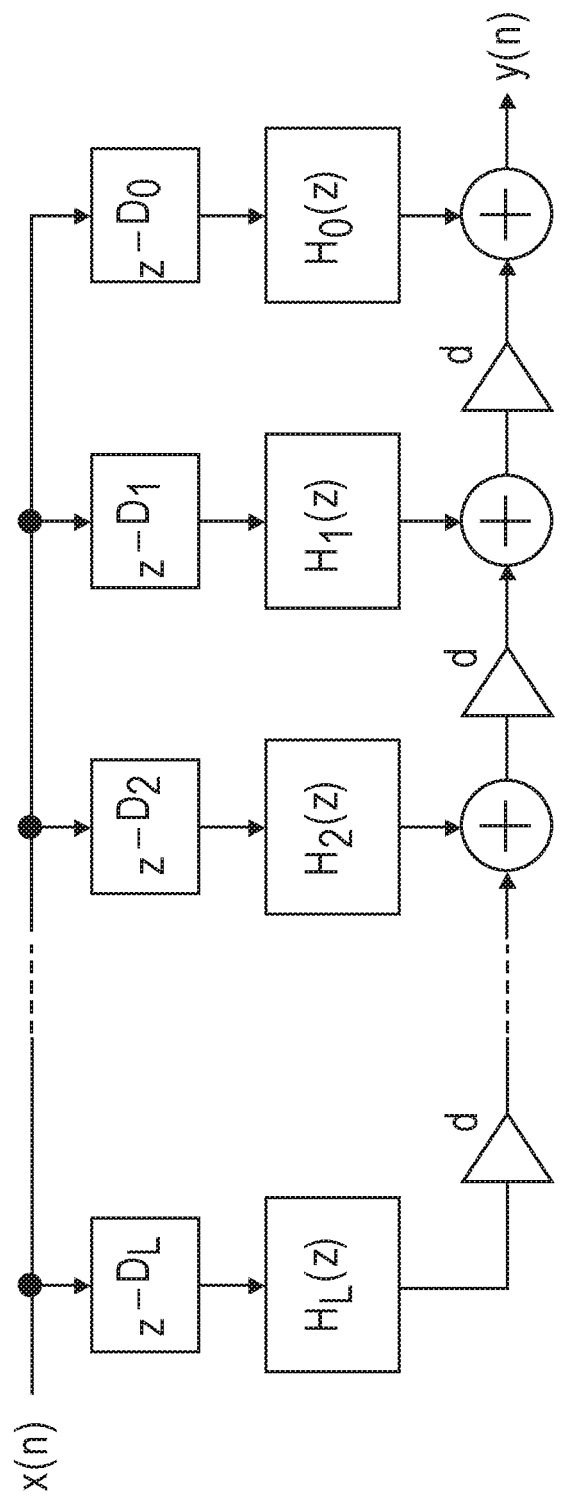
FIG. 9 shows a Farrow architecture.

According to one implementation, one method of approximation uses the Farrow architecture. This a multi-stage FIR summation. One example of a Farrow structure is shown in FIG. 9. One aspect of the structure of FIG. 8 is that the delay adjustment does not affect the FIR definitions. The bank of FIR filters can be calculated once as fixed coefficients. The delay value is varied by a signal variable, d, as shown in FIG. 9. A UABF Farrow structure is also shown in FIGS. 3, 4A and 4B, discussed above.

The Farrow structure as described herein generates optimized filter versions and minimizes the arithmetic operations in the digital domain. Optimized filter versions include designs having different filter definitions, varying numbers of filter sections, and varying numbers of taps per section. According to one implementation, when using a Farrow structure in a Sampled Analog Technology (SAT) implementation, arithmetic operations are passive, which changes the kind of optimizations used.

According to one implementation, a Farrow structure uses SAT circuitry and passive summation. Using SAT circuitry in the Farrow filter increases the number of taps in the filter, but results in an optimization with a wide flat phase bandwidth fraction of Nyquist. According to one example, there are five sections in the Farrow filter (L=5) and each FIR sub-filter is optimized. In various implementations, filter lengths can include varying numbers of taps. In one example, the filter lengths are 27, 9, 27, 11, 19, and five taps. The approximation algorithm results in a wideband fractional delay structure that is flat up to about 0.9 of Nyquist. In another example, the Farrow structure has three sections, the first section on has one capacitor, and the second and third sections each have seven taps. In other examples, the Farrow structure has more than three sections.

According to one implementation, when the parameters of the Farrow structure are varied, the behavior of the structure also varies. In one example, the FIR filters of the structure shown in FIG. 8 have the same length. In various examples, the parameters include:

M=FIR filter order (number of taps is M+1)

N=Farrow structure order (number of FIR filters=N+1, order=N)

K=Prototype filter interpolation ratio

Fpass=FIR lowpass corner frequency (argument to firls function)

Scaling=[ ], list of coefficient scaling applied to each section

The method to generate the FIR coefficients for the Farrow structure is modified for a switched capacitor network. There are several properties of the modified method including:

(1) The passband gain is 0 dB due to the sizes of the coefficients. Note that in methods for generating FIR coefficients in digital network, the passband gain is −6 dB.
(2) The first FIR filter (unity summing path) has a single unit capacitor in it. This means the Farrow order can be increased by one without increasing the area appreciatively. This significantly improves the gain vs frequency performance.
(3) The group delay vs frequency of the method is improved.

Several simulations of Farrow structures yielded the following results:

Simulation Results 1

A series of simulations was run using the following parameter values:
NP=3
M=13
K=128
Fpass=0.81
Scaling=[1, 0.5, 0.8, 0.068]

The gain variation versus frequency is at least four times better than a previous definition and the group delay versus frequency is very small (+−0.002 in 0 to 0.75 frequency range). The gain and phase accuracy are very accurate. In a circuit implementation, the delays are dependent on capacitor values.

In other implementations, optimization techniques are used to reduce the number of taps in the FIR filter bank and to optimize the capacitor size range specific to an SAT implementation.

Simulation Results 2

A second series of simulations used the following parameter values:
NP=2
M=9
K=128
Fpass=0.81
Scaling=[1, 0.95, 0.35]

Reducing NP and M increased the gain and phase errors. This filter definition also results in a significant area reduction as well as power reduction compared to the filter definition of the first simulation.

Simulation Results 3

A further reduction of the value of M shows how this filter architecture performance can be varied by altering the definition. A third series of simulations used the following parameter values:
NP=2
M=7
K=128
Fpass=0.81
Scaling=[1, 0.95, 0.4]

Further reducing M increased the errors in gain and phase. This filter definition also results in a significant area reduction as well as power reduction compared to the filter definition of the second simulation.

Area Estimate

The plot sequence and definition of the Simulation Results 2, with NP=2 and M=9 is used as an example to discuss area. This definition (NP=2, M=9) has 3 fixed coefficient FIR filters, each with 9 taps. The exception to this is the first section, which has a single unity tap in the center when the Laakso method is used to generate the coefficients.

Each of section 2 and 3 uses streaming FIR filters which each have a nine-by-nine array of tiles. Each tile is sized for a maximum unit cap size of 0.5 pF (pF=picofarads). Each tile is estimated to be 14.1 um×29.8 um (um=micrometer). The integer delay ring unit cap is 0.5 pF also.

TABLE 1

Single Channel Beamformer and delay area, Unit cap = 1 pF.

| Block Name | Tile array Size | Area (ku$^2$), 1 channel | Area (mm$^2$), 128 channel |
|---|---|---|---|
| FIR bank | 2 × 9 × 9 + 1 | 76.3 ku$^2$ | 9.76 |
| Delay Ring | 200 | 53.8 ku$^2$ | 10.76 |
| Strobe generator | 1 | | 1.92 |
| Total | | 194 ku$^2$ | 22.44 |

Integer Delay Size

The area estimate above is for the fractional delay component of the delay-and-sum block and the integer delay block using SAT for 128 channel system. The estimate assumes a maximum integer delay of 200 samples as $f_s$=4*fc. This number is determined as described below.

The integer delay can be the integer delay difference for the vector paths being summed to create the compressed low resolution image (LRI) data. The total time or time-of-flight (TOF) is determined by the distance and velocity. In one implementation, the distance is between 10 mm and 80 mm with a lateral range of +−13 mm. According to one implementation, the window is 5 mm to 35 mm and there is +−7 mm lateral range.

The maximum total TOF is:

TOF(max)=2*0.08 m/1540 m/s=2*52 us=104 us, where sound velocity is 1540 m/s.

The maximum TOF delta happens at near targets since it depends on the angles:

Delta-TOF(max)=2*(sqrt(26^2+10^2)−10) mm/1540 m/s=2*0.018 m/1540 m/s=~23 us

The minimum TOF delta happens at far targets:

Delta-TOF(min)=2*(sqrt(26^2+80^2)−80) mm/1540 m/s=2*0.004 m/1540 m/s=~5.4 us

The minimum and maximum TOF delta numbers indicate that the bulk of the delay is common to all the transit paths in the sum for a single point. The common delay can be done in the digital domain by referencing delayed values of the compressed data after the ADC.

The difference between the minimum and maximum TOF deltas of ~18 us can be implemented as a bank of capacitor analog memory that the Farrow structure FIR filters address. In one example, if the sample rate is 40 MHz, then the integer delay is 714 memory elements.

However, if the dynamic receive focus uses a constant F-number (F #), then at near locations (which have maximum delta TOF times) the number of elements used for the receive focus is reduced to maintain the constant F #. At the nearest distance of 10 mm, the aperture would be reduced and this reduces the maximum delta TOF.

Transducer pitch=Lambda=c/f, for 7 MHz center frequency Lambda=0.22 mm, where c=1540 m/s At maximum distance F #=Depth/Aperture=80 mm/192*0.22 mm=~1.9

At minimum distance the aperture becomes Depth/F #=10 mm/1.9=~5 mm

So the new maximum TOF delta becomes:

Delta-TOF(max)=2*(sqrt(5^2+10^2)−10) mm/1540 m/s=2*0.001 m/1540 m/s=~1.3 us

In one implementation, the difference between the minimum and new maximum TOF deltas of ~4 us is implemented as a bank of capacitor analog memory that the Farrow structure FIR filters address. In one example, the sample rate is 40 MHz and the integer delay is 164 memory elements. In another example, the sample rate is $4*f_c$=28 MHz and the integer delay is 112 memory elements.

Figure 10:
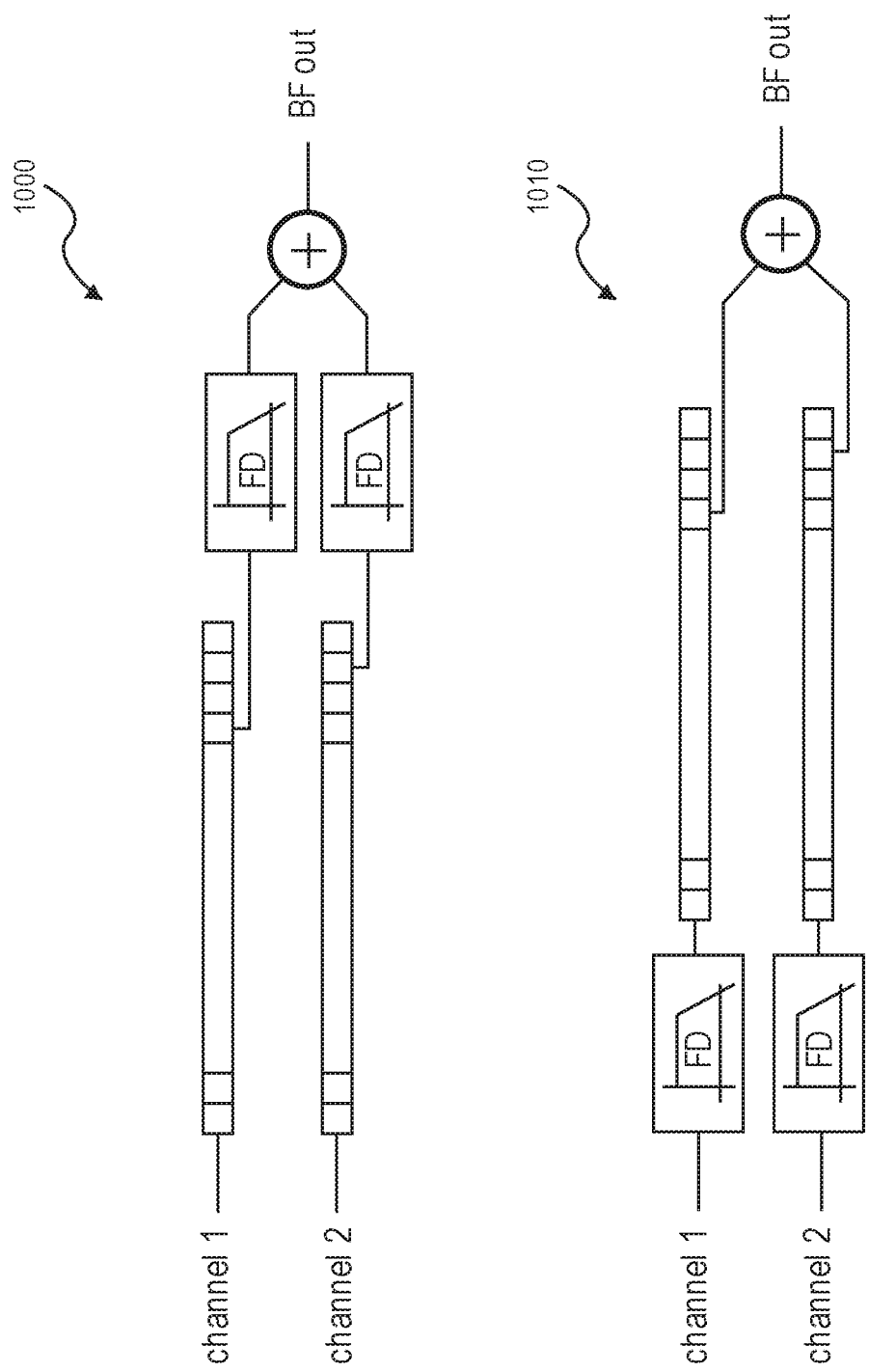
FIG. 10 two alternative system designs including a delay line and a Farrow filter, according to some embodiments of the disclosure.

FIG. 10 shows two alternative system designs. In one implementation, shown in the top design, a system design 1000 includes a configurable delay line of up to 200 samples followed by an analog memory array to run the FIR filters in the Farrow structure. In another implementation, the delay line and the Farrow filter are interchanged. As shown in the bottom design, the system design 1010 includes a Farrow filter is first, followed by a configurable delay line. According to one implementation, the two implementations shown in FIG. 10 can be made equivalent at the BF output.

One benefit of having the FD filter first is the interface between the delay and FD filter. The entire structure is passive without an active buffer stage between the delay line and FD filter. In terms of capacitance size, the delay line element has much less capacitance than the total input or output capacitance of the FD filter. Therefore, having the delay line first means it has to charge share (CS) to the input capacitance of the FD filter, which introduces attenuation. However, when the FD filter is first, it becomes possible to integrate the delay line elements into the FD filter, which eliminates attenuation due to charge sharing.

According to one implementation, the two architectures have the same output values. One significant difference between the two architectures is that the application of the integer and fraction values happens at different times, and the integer and fraction values are organized differently in memory for the two architectures.

Power Estimate

According to one implementation, using the definition in Table 1 and basing power scaling on the measured power of the TDF0 device, the power requirements can be (grossly) estimated. In one example, the delay filters are clocked at 40 MHz sample rate. The actual clock rate is 80 MHz at least to provide clock phases for switching strobes.

Another SAT development of a low pass filter (LPF) is used to estimate the power for the design. In the design, the Register Transfer Language (RTL) generates strobes for a 224 LPF. It runs as a block rate filter. However, the digital strobe generator logic is generating row and column strobes for the SAT designs. That block consumes approximately 4.3 uA/MHz sample rate. Since it will be running at 80 MHz clock input rate the current consumption per channel is doubled to 4.3*2*40 uA/channel=344 uA/channel. At 3.3V VDD this is 1.1 mW/channel.

However, because the digital strobes used for each channel are the same, the power can be reduced by sharing one digital strobe generator. The analog VDD current is dependent on signal size but at 1Vrms signal it is about 200 uA/channel or about 0.66 mW/channel at 3.3V VDD. According to one example, because of the severe attenuation of the transmit pressure wave, the 1Vrms average receive signal is very conservative.

There is still a single ADC for the three-by-three beamformed output running at 40 Msps. In one example, an 16-bit ADC has a power dissipation of 200 mW at 1.8V Vdd. The power estimate is summarized below in Table 2.

TABLE 2

Summary of Power Estimate

| Block | Current | Power |
| --- | --- | --- |
| 1 channel UABF - digital | 344 uA | 1.1 mW, 3.3 V |
| 1 channel UABF - analog | 200 uA | 0.66 mW, 1 Vrms |
| Total 1 channel | 544 uA | 1.76 mW |
| ADC | 1,100 uA | 200 mW, 1.8 V |
| Total 128 channels + ADC | 71 mA | 425 mW |

Another part of the power consumption is another digital block that generates the delay profiles and sets the register values in each channel. This digital block will add to the power consumption and the total module power.

FD Circuit Design

Figure 11A:
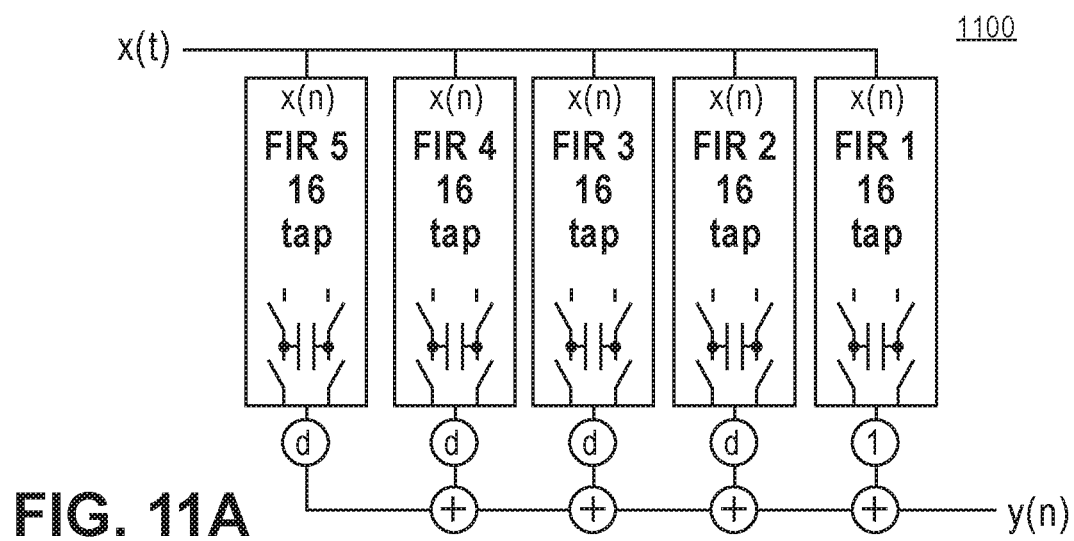
FIGS. 11A-11C show Farrow filter designs, according to some embodiments of the disclosure.

One of property of the Farrow filter architecture is that it can change the fractional delay value dynamically by changing a single variable value. FIG. 11A illustrates a Farrow filter architecture 1100 including five FIR tap. This filter design can be modified to change the variables.

Figure 11B:
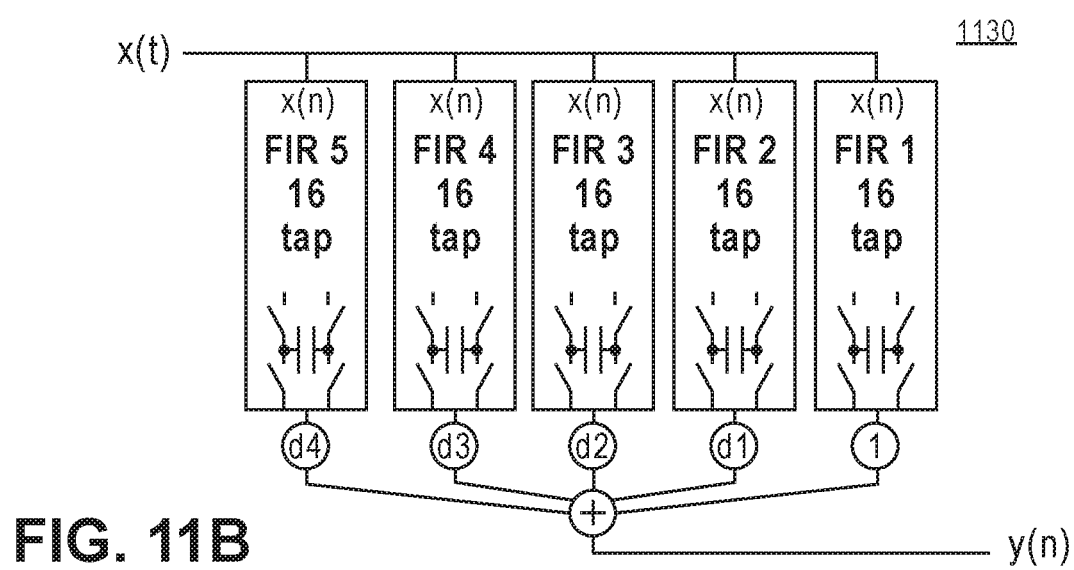

FIG. 11B is a second Farrow filter architecture 1130 including five FIR taps, according to some embodiments of the disclosure. The second Farrow filter architecture 1130 includes variables d1, d2, d3, and d4. When variables d1, d2, d3, d4 are: d1=d, d2=d^2, d3=d^3, and d4=d^4, the Farrow filter architecture 1130 has the same function as the Farrow filter architecture 1100. The circuit implementation of the design of the Farrow filter architecture 1130 of FIG. 11B is discussed below, under the "FIR design" heading, which includes discussion on the design of the FIR output scaling variables, d1 through d4.

A simulation results for various designs of the Farrow filter are discussed herein. One specific example will be used for the two sections that follow so actual coefficient values and capacitor values can be defined. The design example will be based on the NP=2, M=9 parameters. The performance for this configuration is discussed above the section titled "Simulation Results 2". This example demonstrates the properties of the design for a single channel FD filter.

FIR Design

The FIR design as shown in FIGS. 11A and 11B is the same as other implementations of SAT FIR filters. Each of the FIR sections except for section 1 is an M×M array of tiles to implement a streaming FIR filter.

The design of the coefficients for the FIR sections can be done in many ways. However, present methods are designed for digital filter implementations and not analog SAT structures. Systems and methods for implementing the Farrow structure as a switched capacitor (switchcap) circuit structure are described herein.

According to another implementation, Linear Programming methods are used to optimize the coefficient values based on constraints of the required performance. The principle constraint is that this method includes a fixed range of capacitor values that represent the coefficient values. In practical terms, the capacitors can be manufactured over a finite range of values. In particular, the smallest capacitor is determined by the process design and layout rules. An example of the filter coefficients is shown in Table 3 below:

TABLE 3

Coefficients for NP = 2, M = 9

| Section 0 | Section 1 | Section 2 |
|---|---|---|
| 0.0000 | 0.0674 | −0.0025 |
| 0.0000 | −0.1579 | 0.0093 |
| 0.0000 | 0.3392 | −0.0328 |
| 0.0000 | −0.9499 | 0.2056 |
| 1.0001 | 0.0000 | −0.3603 |
| 0.0000 | 0.9505 | 0.2057 |
| 0.0000 | −0.3394 | −0.0326 |
| 0.0000 | 0.1582 | 0.0093 |
| 0.0000 | −0.0674 | −0.0025 |

The normalization is:

$$a \text{ max} = 0.9951 \; 0.8904 \; 3.9001$$

The variable amax represents the scaling used to determine the original filter coefficient values from the normalized capacitance values. This scaling is used when the output charge scaling is completed with the second CS event.

Output Scaling

One of the core properties of SAT filter design is the ability to charge share between multiple filter outputs to make more complex behavior. The Farrow filter design is one example. The implementation of the Farrow filter is a design method that reduces area and power for FD filters.

Figure 11C:
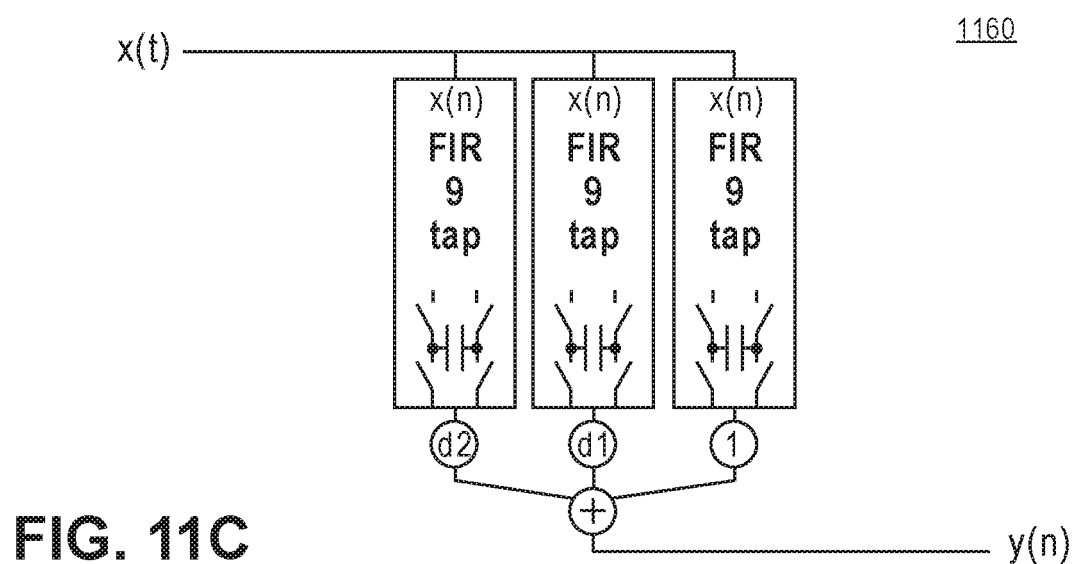

The implementation of the Farrow filter using SAT circuits is shown herein in FIGS. 4A and 4B. According to one example, FIG. 11C is a simplified version of FIG. 11B. In this case, NP=2 and M=9. Table 3 shows the coefficient values. Note that the values for the $1^{st}$ section are zero except for the center value. In FIG. 11C, the $1^{st}$ section is summed with a weight of 1. Each of the second and third sections has nine values or nine capacitors.

Referring to FIGS. 11A-11C, after all of the capacitors in a section are connected together to make the next output, they all have the same voltage across them. But the charge on them is proportional to the capacitor or coefficient size. Thus, if one or more of the coefficient capacitors to the FIR output node is disconnected, the available charge is proportional to the sum of the remaining capacitors still connected together. The fraction of total charge can have many values based on all of the possible states of the nine capacitors and coefficients. There are 2^9−1 possible states of the capacitor sets.

According to one implementation, the scaling can be done for each section (except the first section which has a weight of 1). The scaling of d1 and d2 shown in FIGS. 11B and 11C depends on the delay value. The delays are uniform fractions of a sample period.

According to various implementations, the method of mapping the charge scaling using a subset of coefficient capacitors may result in errors. For example, the FIR filter coefficients may not give exact values for the delay scaling.

Ultrasound Analog Beamforming Circuit (UABF)

The UABF block is a single passive multi-step charge sharing signal path as described above with respect to FIGS. 4A and 4B. According to some examples, the circuit diagram can be used to plan timing and layout for the filter. According to one example, the definition of the fractional delay filter includes the following parameters (these are the parameters used in the section titled "Simulation Results 2" above):

1. Laakso method for coefficient design.
2. N=9 (number of taps in FIR sections).
3. NP=2 (filter order). Number of sections is NP+1.
4. K=128.
5. Fpass=0.81*Nyquist.
6. Coefficient scaling={1,0.95,0.35}
7. Lowlimit=0.01 (smallest capacitor coefficient). Smaller values=0. This spec is normalized to 1.0
8. Maximum sample rate=40 MHz.
9. 2V or 3V signal path.

According to some examples, as described above, each channel has three FIR filters that sample the same input waveform. The first section has a single unit capacitor in the center, while the second and third sections have multiple capacitors. The three FIR filters are connected together to form the channel delayed output. The 128 channels are connected together to form the beamformed single output charge.

Figure 12:
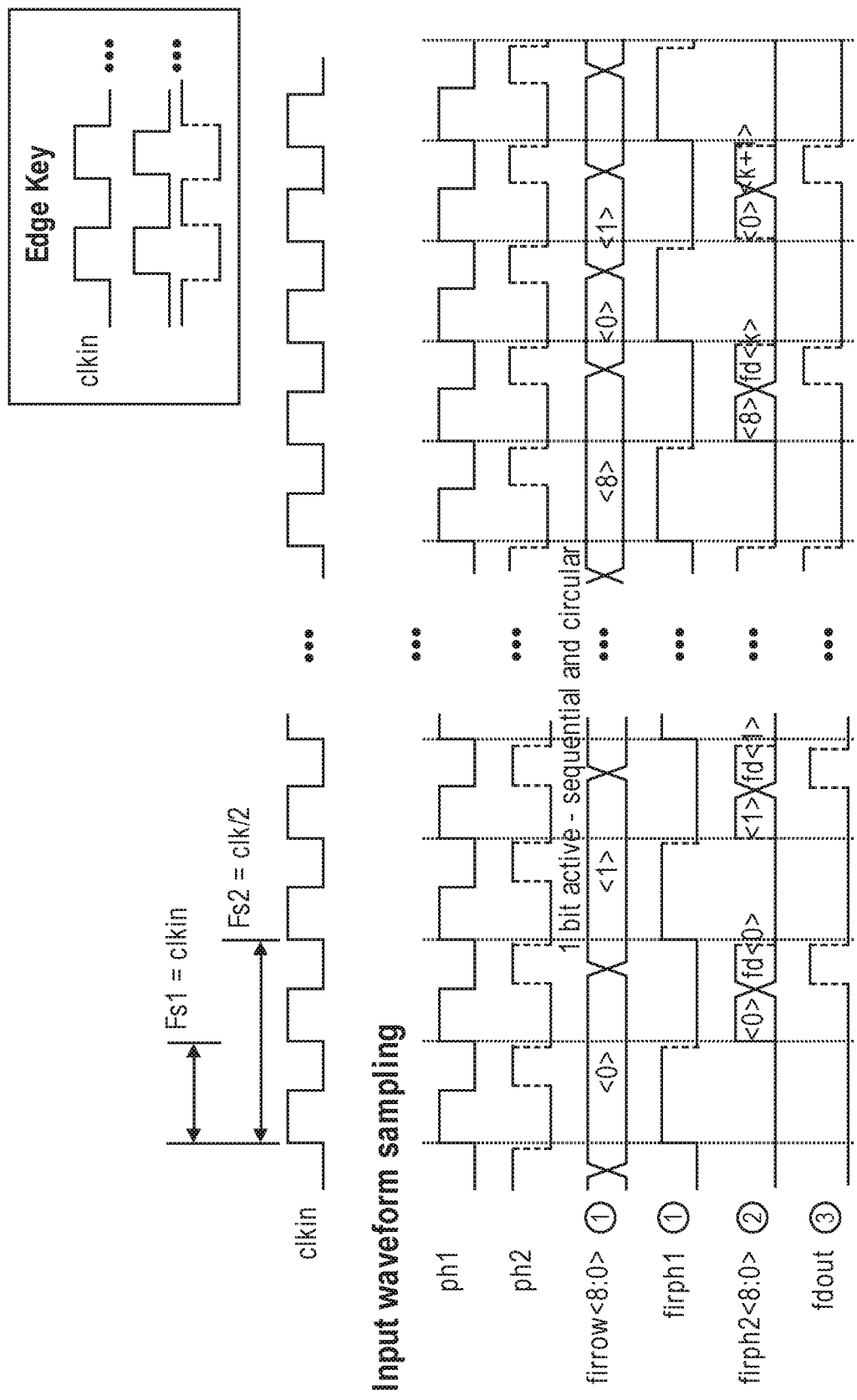
FIG. 12 shows a timing diagram for the UABF system of FIG. 4A, according to some embodiments of the disclosure.
Figure 12:
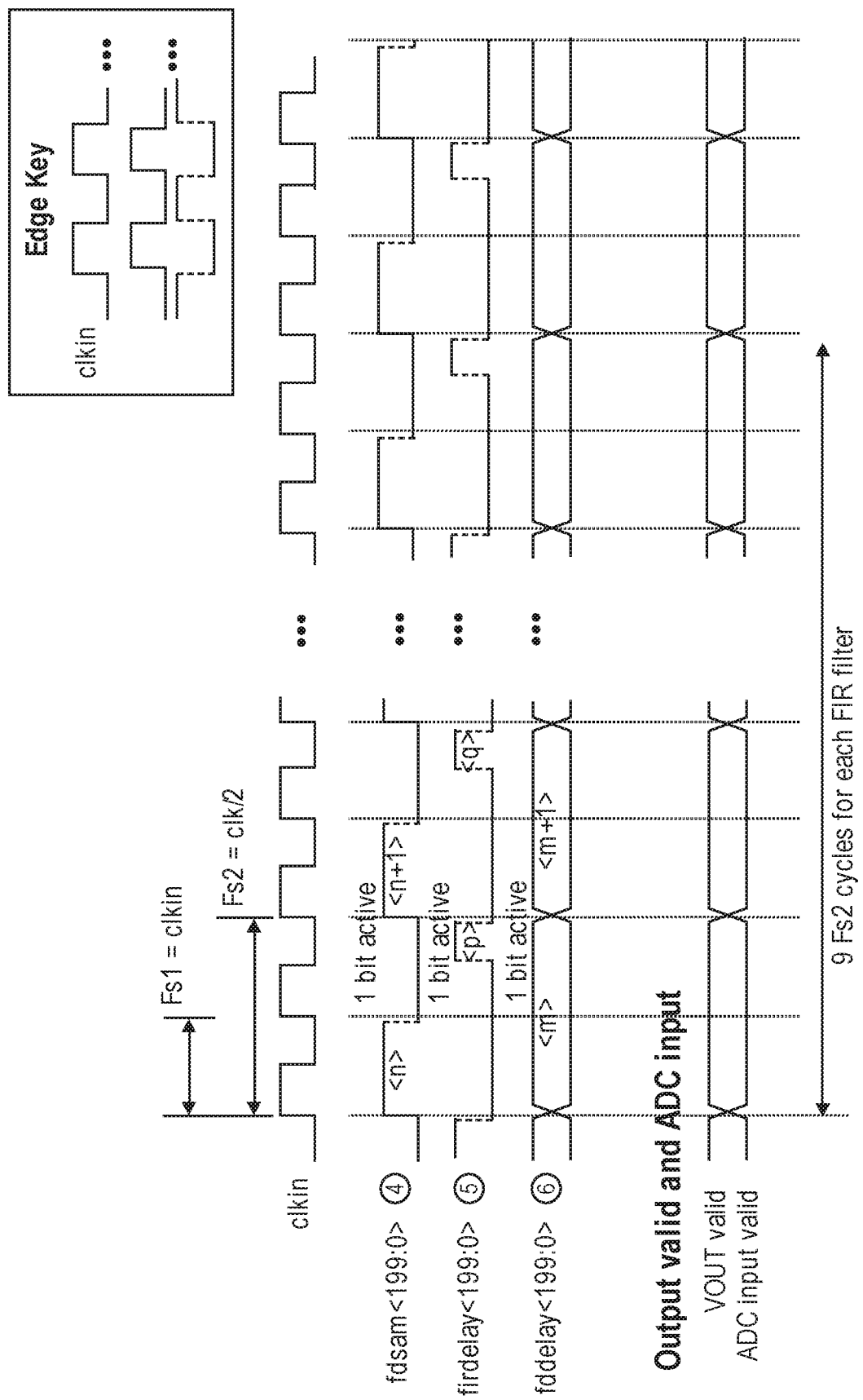

FIG. 12 shows the timing and the strobe numbers reference the labeled switches in FIG. 4B. The following sections describe the input and output characteristics.

Input Sampling

The UABF is a sampled analog signal processor and the input sampling determines the time period of sampling. The input sampling happens when the strobe firph1 is active high as shown in FIG. 12. The strobe firph1 is active for one half of a clock period. In one example, this is a minimum of about 12 ns duration for the 40 MHz maximum input sample rate. The UABF driver settles within this time. In one example, the total input capacitance of a UABF design as shown in FIG. 4B is about 5.6 unit capacitors, or about 5.6 pF using a 1 pF unit capacitance value. In one implementation, the capacitance is constant, but the load is a switched capacitor load and only seen when firph1=1. When firph1=0 the load comprises minimal switch and wiring parasitic capacitance. In other implementations, the load appears constant over time, and can also appear constant over samples.

Output Sampling

As seen in FIG. 12, the output is valid when strobe 6, Vout, is high, for approximately one sample clock period, according to some implementations. According to one implementation, one property of the circuit is that the output value is represented as charge, not voltage. The capacitance that holds the output charge changes for each fractional delay value. The variation of the output capacitance is about 30% and the capacitance is around 3.1 pF to 4.5 pF for a delay increment of 0.125. In one example, there are 8 possible fractional delay values within one sample time period. A compensation capacitor functions to make the total capacitance at the output constant for all delay values. The output charge is unchanged since this capacitor is reset every sample cycle. According to one example, the compensation capacitor is not used when the ADC input is charge-based and not voltage based.

According to other implementations, the output value is represented as voltage.

Integer Delay

FIG. 4B shows the FD filter and the integer delay integrated into a single passive circuit design, according to some implementations. The delay line is the top right corner of the Farrow filter. The integer delay is implemented as an array of unit capacitors with input switches that can point to any delay element and separate output switches that can point to any delay element.

An addressed delay element is integrated into the Farrow FD filter by acting as the single unit capacitor of the first section. In some implementations, the first section, as discussed previously, is designed to be a single unit capacitor and zeroes elsewhere. In other implementations, the first section is a full FIR capacitor. In some examples, the first section is a full FIR capacitor, and a unit delay capacitor is one of the capacitors in the first section. In some examples, the unit delay capacitor can be used for unit capacitors in other sections. In other examples, the first section is a full FIR capacitor, and the unit delay capacitor is one of the capacitors in a different section.

UABF Performance

According to various implementations, comparisons of models of the generalized UABF circuit with digital Beamforming show that the UABF performs about equally as well as the digital BF. A comparison of ideal, linear, and UABF Farrow interpolation methods for the beam properties indicates that the UABF performance is nearly identical to the ideal (floating point) beam plot. The linear interpolation is significantly worse than the UABF Farrow.

Digital Memory

According to various implementations, in practice the actual implementation of the structures discussed herein may include only switches and capacitors. However, switches and capacitors have non-ideal properties such as switch resistance and capacitor mismatch. In addition, parasitic capacitance may affect behavior. Another aspect of the design is the memory requirements for the dynamic focusing requirements. In one example, when there is a different set of delays for every time point, the total memory can be estimated:

$$\text{Max transition time} = 2*150 \text{ mm}/c = \tilde{~}200 \text{ us} = \tilde{~}8000$$
$$\text{samples at maximum } Fs \text{ of } 40 \text{ MHz}$$

If a single delay variable is 4 bit binary (16 possible values) then 8000 samples is 4 k Bytes per element.

If the transducer is 192 elements then maximum total memory is 768 k Bytes

According to various examples, 768 k is a reasonable amount of memory, and there are a number of ways it can be implemented. In one example, if the digital delay value set is sent to the UABF device using a single serial port, the data rate for real time imaging is about 30 Gbit/s. For reference, a USB 3.1 can provide up to 10 Gbit/s.

In other implementations, the delay profiles are generated on the fly with an approximation algorithm. In one example, the approximation algorithm can make straight linear approximations of the delay profiles and implement delta behavior. In another example, the approximation algorithm moves delay profile state as changes rather than as explicit delay values. In some implementations, the delays are fixed (constant). In other implementations, the delays vary a few times during the receive time after the transmit event.

Apodization

Figure 13:
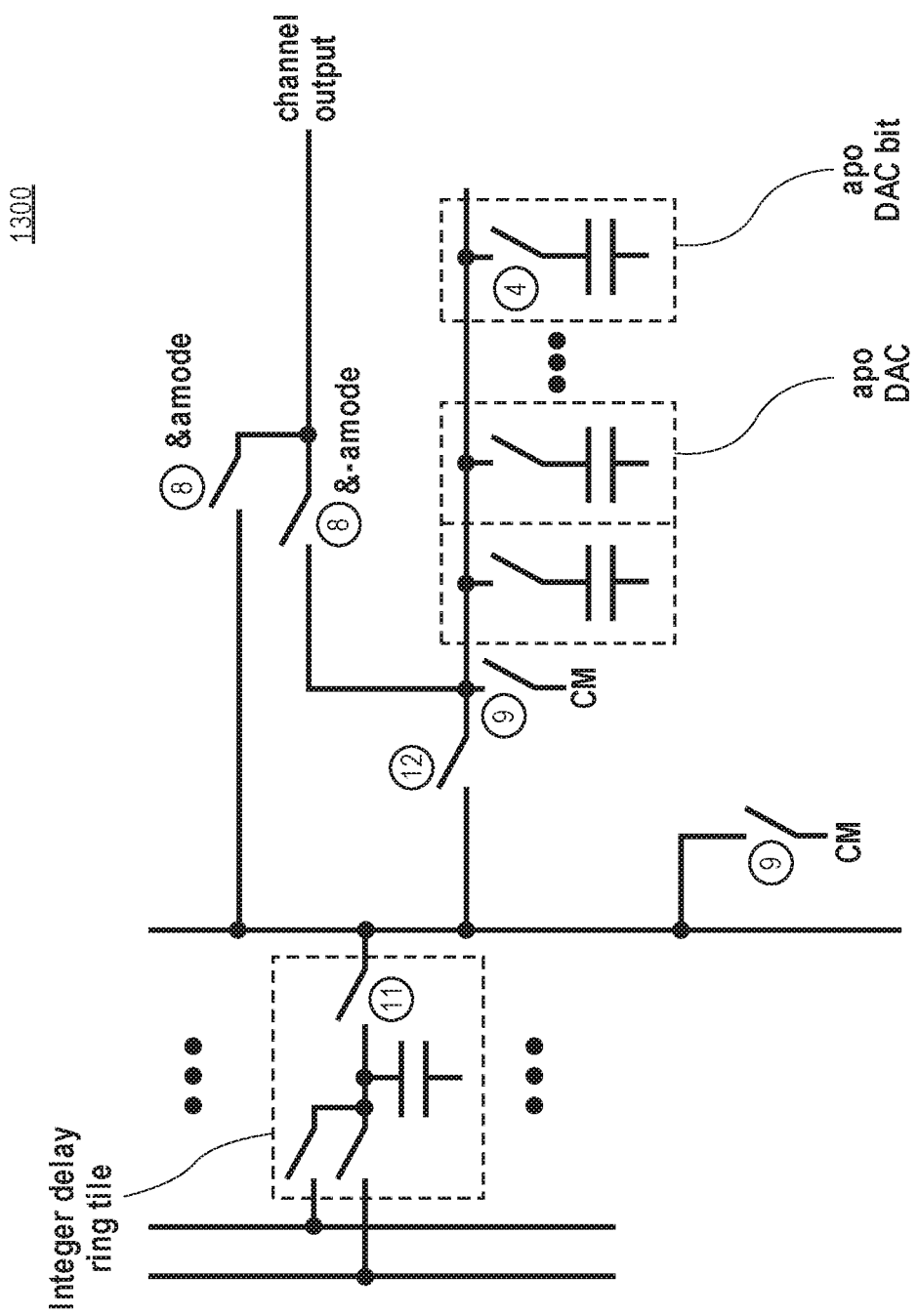
FIG. 13 shows an apodization circuit, according to some embodiments of the disclosure.

FIG. 13 shows an apodization circuit 1300, according to some embodiments of the disclosure. Apodization is the spatial windowing of the input waveforms to reduce sidelobes. According to one example, this is analogous to the windowing method for FIR filter design. The window is a weighting shape, such as the hamming window, applied across the physical transducer elements at each time step. Sidelobe height is a FOM for beamforming, and apodization is used to reduce sidelobes. One method to add apodization is to add another CS event between the input signal at each element and the Farrow FD filter (or other interpolation) which scales the aperture elements by a Gaussian-like window shape to reduce the effects of the rectangular window signal shape. This additional CS event before the sampling of the FIR sections of the FD filter can be fixed or programmable.

According to some implementations, for an ultrasound imaging application, the windowing or apodization is spatial, across the active transducer elements. In some examples, spatial apodization occurs across the aligned samples of the active elements. Thus, the apodization occurs after the integer and fractional delay operation.

Figure 14:
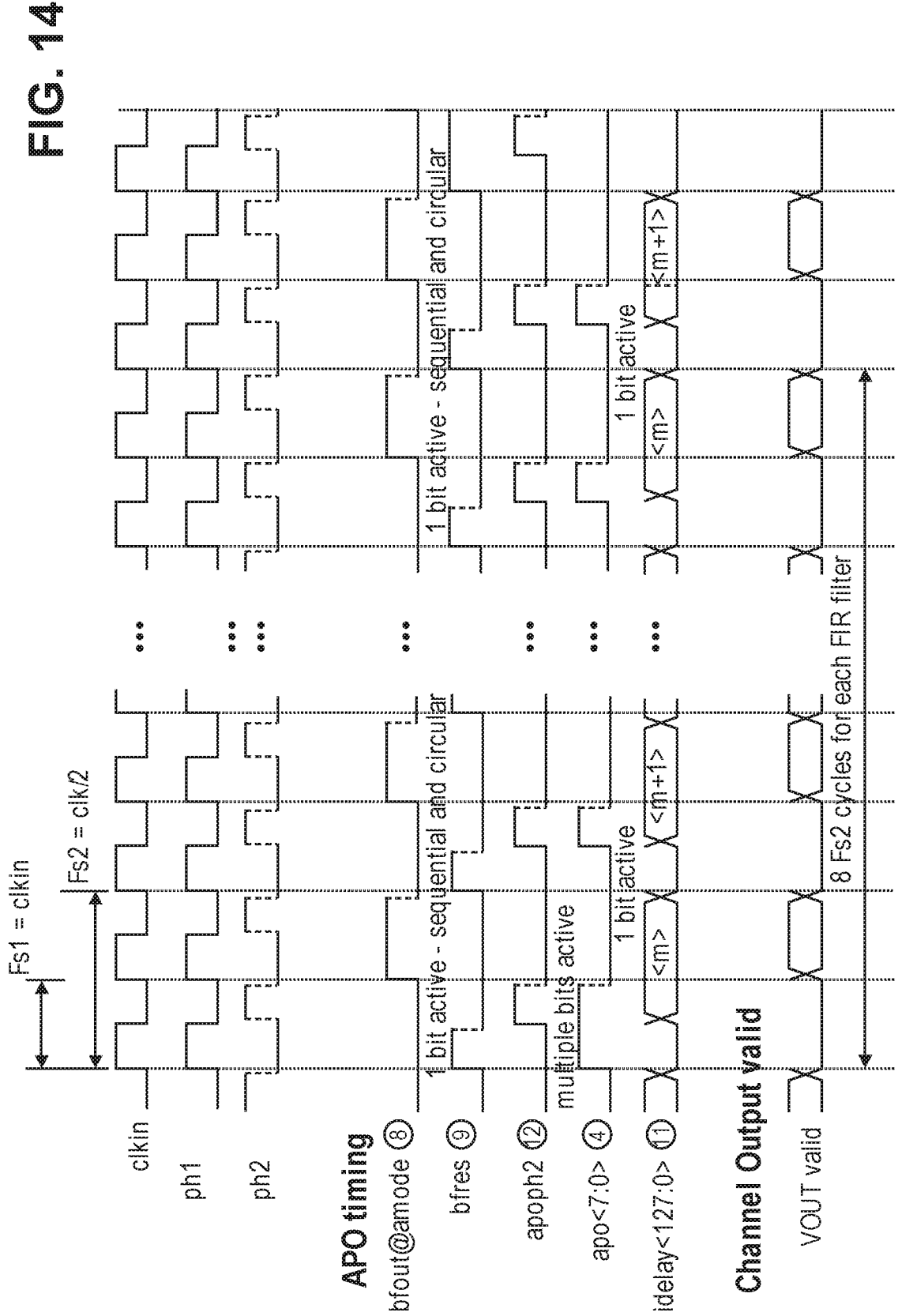
FIG. 14 shows a timing diagram for the apodization circuit of FIG. 13, according to some embodiments of the disclosure.

The timing for the apodization operation is shown in FIG. 14. There are three steps to the apodization charge scaling.

1. Set apodization DAC state, reset apodization DAC capacitors, and reset parasitic capacitors. Strobe (4), (9)
2. Charge share between selected integer delay tile and apodization DAC. Strobe (12)
3. Connect output node to either integer delay output or apodization DAC output depending on amode state. Strobe (8)

In one implementation, the design defines the apodization DAC as 5 bits or 32 LSB tiles. The capacitance in each least significant bit (LSB) tile depends on the unit capacitance of the farrow filter such that the scaling can be linearized to 5 bits of resolution. In one example, linearizing the apodization scaling involves mapping the 6 bits of state (5 DAC bits and the amode bit state) or 64 states to fit a linear straight line scaling from 0 charge to maximum charge on integer delay tile cap.

According to one implementation, the DAC is acting as a charge sharing event, and thus, the charge scaling used for the apodization is not linear for the DAC codes. Thus, there is a mapping between the apodization value and the actual DAC code.

UABF Applications

According to various implementations, the number of channels, delays, apodization and other parameters in the UABF circuit can be optimized for many uses. Some examples are included below.

Channel Count

Many of the examples in this document refer to a linear array of 128 elements. This transducer construction is very common for a high quality image, but there are many other methods of constructing the transducer, and linear array could be any selected size. According to one example, another transducer example is a linear type array having several rows or elements to allow focusing the beam on the y-axis. The linear type array may be a 1.5D, a 1.75D or another type of array. According to other examples, 2D arrays are used. 2D arrays are N×N arrays of elements, often several thousand elements total, that allow construction of 3D and 4D imaging. The physical construction of these arrays is difficult and requires some electronics behind each element because of the sheer number of channels and the need to decimate the information as soon as possible. This decimation is presently done a partial BF of sub-arrays of elements. According to some examples, the UABF is good for this design and construction.

Delay Profile

In various implementations, the delays discussed in many parts of the specification that are required for the focus and steering can be either fixed or programmable after a transmit event and during receive of that transmit event.

Sub-Aperture Beamforming

According to various implementations, the descriptions refers to a BF method for a finite group of transducer elements (or any other set of independent signals). However, the finite group of elements can be all or a part of a specific transducer at any time sample. In particular, there can be multiple BF blocks that form beams for a sub-group of elements. For a 128 element transducer there can be 4 UABF blocks that look at each of the 32 elements sub-groups of elements, either contiguously or interleaved.

Parallel Receive Beamforming

A number of applications of ultrasound image data use fast image updates or fast frame rate values. To increase the frame rate, the UABF hardware can be duplicated multiple times to create simultaneous BF outputs. This is referred to as Parallel Receive Beamforming. The frame rate is directly increased by the number of UABF blocks. In various examples, using 2 UABF blocks increases frame rate by two times the original frame rate, using 4 UABF blocks increases frame rate by four times the original frame rate, and 8 UABF blocks increases frame rate by eight times the original frame rate.

Synthetic Aperture Imaging

Synthetic aperture imaging potentially results in higher quality images with same number of elements. Synthetic Aperture (SA) imaging is based on delay-and-sum BF that the UABF can provide. FIG. 41 shows a diagram of an example of SA imaging. The first step is delay-and-sum beamforming to create many low resolution images. The low resolution images are combined in many ways to make a high resolution image. The UABF can be implemented to support SA imaging by a specific design or a configuration of a general purpose implementation.

Multiplexed BF

One of the properties of the SAT implementation is the fast calculation speed to perform the beamforming. In digital implementation this calculation is done by clocked hardware and the speed is limited by how much hardware is implemented versus serially multiplexing a calculation engine, for example. In the UABF domain the entire calculation is done after 3 CS events. These events can happen very quickly depending on semiconductor process used. This speed means an architecture can be implemented that uses the same physical UABF block that is multiplexed many times either across multiple transducer elements sub-groups or the same elements multiple times. This is accomplished by an input switching matrix that steers the UABF inputs to multiple groups of inputs.

Figure 15:
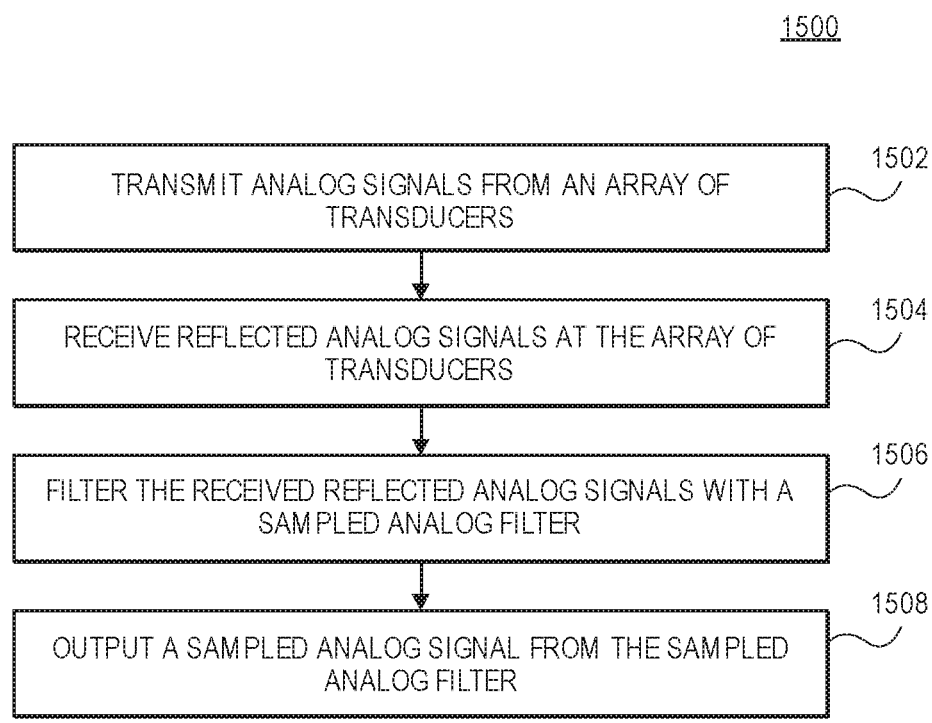
FIG. 15 shows a flow chart of a method for sampled analog beamforming, according to some embodiments of the disclosure.

FIG. 15 shows a flow chart of a method 1500 for ultrasound analog beamforming, according to some embodiments of the disclosure. The method 1500 includes, at step 1502, transmitting analog signals from an array of transducers. At step 1504, reflected analog signals are received at the array of transducers. At step 1506, the received reflected analog signals are filtered with a sampled analog filter. At step 1508, the sampled analog filter outputs a sampled analog signal. Filtering includes adding a delay to each of the received analog signals. According to one example, the delay includes a fractional delay and an integer delay.

In some implementations, after step 1508, the method 1500 includes windowing, at an apodization circuit, a waveform of the sampled analog signal to reduce sidelobes. In some examples, after step 1508, the method 1500 includes adding, at a summation node, the sampled analog signal to parallel sampled analog signals from parallel sampled analog beamformers.

Other Applications

According to various implementations, sampled analog technology can be used in any ultrasound, radar, and acoustics applications for low power beamforming. SAT can be a building block for advanced ultrasound beamforming applications including synthetic aperture techniques, plane wave imaging, divergent beamforming, retrospective dynamic transmit focus applications, and subaperture array beamforming. SAT can be used in beamforming applications in probes, including single-row (1D) ultrasound probes, and multi-row probes (1.5D, 1.75D, and 2D arrays), as well as catheter probes. SAT can be used in both probe and console (system) beamforming applications, including applications that require very low power, as well as high density applications. SAT beamforming can also be used in wearable ultrasound device form factors that incorporate beamforming.

According to some implementations, SAT beamforming can be used for identity and security applications such as body part imaging. In some examples, SAT beamforming can be used for fingerprint imaging. In other examples, SAT beamforming can be used retinal imaging.

Variations and Implementations

In the discussions of the embodiments above, the capacitors, clocks, DFFs, dividers, inductors, resistors, amplifiers, switches, digital core, transistors, and/or other components can readily be replaced, substituted, or otherwise modified in order to accommodate particular circuitry needs. Moreover, it should be noted that the use of complementary electronic devices, hardware, software, etc. offer an equally viable option for implementing the teachings of the present disclosure.

In one example embodiment, any number of electrical circuits of the FIGURES may be implemented on a board of an associated electronic device. The board can be a general circuit board that can hold various components of the internal electronic system of the electronic device and, further, provide connectors for other peripherals. More specifically, the board can provide the electrical connections by which the other components of the system can communicate electrically. Any suitable processors (inclusive of digital signal processors, microprocessors, supporting chipsets, etc.), computer-readable non-transitory memory elements, etc. can be suitably coupled to the board based on particular configuration needs, processing demands, computer designs, etc. Other components such as external storage, additional sensors, controllers for audio/video display, and peripheral devices may be attached to the board as plug-in cards, via cables, or integrated into the board itself. In various embodiments, the functionalities described herein may be implemented in emulation form as software or firmware running within one or more configurable (e.g., programmable) elements arranged in a structure that supports these functions. The software or firmware providing the emulation may be provided on non-transitory computer-readable storage medium comprising instructions to allow a processor to carry out those functionalities.

In another example embodiment, the electrical circuits of the FIGURES may be implemented as stand-alone modules (e.g., a device with associated components and circuitry configured to perform a specific application or function) or implemented as plug-in modules into application specific hardware of electronic devices. Note that particular embodiments of the present disclosure may be readily included in a system on chip (SOC) package, either in part, or in whole. An SOC represents an IC that integrates components of a computer or other electronic system into a single chip. It may contain digital, analog, mixed-signal, and often radio frequency functions: all of which may be provided on a single chip substrate. Other embodiments may include a multi-chip-module (MCM), with a plurality of separate ICs located within a single electronic package and configured to interact closely with each other through the electronic package. In various other embodiments, the filtering functionalities may be implemented in one or more silicon cores in Application Specific Integrated Circuits (ASICs), Field Programmable Gate Arrays (FPGAs), and other semiconductor chips.

It is also imperative to note that all of the specifications, dimensions, and relationships outlined herein (e.g., the number of processors, logic operations, etc.) have only been offered for purposes of example and teaching only. Such information may be varied considerably without departing from the spirit of the present disclosure, or the scope of the appended claims. The specifications apply only to one non-limiting example and, accordingly, they should be construed as such. In the foregoing description, example embodiments have been described with reference to particular processor and/or component arrangements. Various modifications and changes may be made to such embodiments without departing from the scope of the appended claims. The description and drawings are, accordingly, to be regarded in an illustrative rather than in a restrictive sense.

Note that the activities discussed above with reference to the FIGURES are applicable to any integrated circuits that involve signal processing, particularly those that can execute specialized software programs, or algorithms, some of which may be associated with processing digitized real-time data. Certain embodiments can relate to multi-DSP signal processing, floating point processing, signal/control processing, fixed-function processing, microcontroller applications, etc.

In certain contexts, the features discussed herein can be applicable to medical systems, scientific instrumentation, wireless and wired communications, radar, industrial process control, audio and video equipment, current sensing, instrumentation (which can be highly precise), and other digital-processing-based systems.

Moreover, certain embodiments discussed above can be provisioned in digital signal processing technologies for medical imaging, patient monitoring, medical instrumentation, and home healthcare. This could include pulmonary monitors, accelerometers, heart rate monitors, pacemakers, etc. Other applications can involve automotive technologies for safety systems (e.g., stability control systems, driver assistance systems, braking systems, infotainment and interior applications of any kind). Furthermore, powertrain systems (for example, in hybrid and electric vehicles) can use high-precision data conversion products in battery monitoring, control systems, reporting controls, maintenance activities, etc.

In yet other example scenarios, the teachings of the present disclosure can be applicable in the industrial markets that include process control systems that help drive productivity, energy efficiency, and reliability. In consumer applications, the teachings of the signal processing circuits discussed above can be used for image processing, auto focus, and image stabilization (e.g., for digital still cameras, camcorders, etc.). Other consumer applications can include audio and video processors for home theater systems, DVD recorders, and high-definition televisions. Yet other consumer applications can involve advanced touch screen controllers (e.g., for any type of portable media device). Hence, such technologies could readily part of smartphones, tablets, security systems, PCs, gaming technologies, virtual reality, simulation training, etc.

Note that with the numerous examples provided herein, interaction may be described in terms of two, three, four, or more electrical components. However, this has been done for purposes of clarity and example only. It should be appreciated that the system can be consolidated in any suitable manner. Along similar design alternatives, any of the illustrated components, modules, and elements of the FIGURES may be combined in various possible configurations, all of which are clearly within the broad scope of this Specification. In certain cases, it may be easier to describe one or more of the functionalities of a given set of flows by only referencing a limited number of electrical elements. It should be appreciated that the electrical circuits of the FIGURES and its teachings are readily scalable and can accommodate a large number of components, as well as more complicated/sophisticated arrangements and configurations. Accordingly, the examples provided should not limit the scope or inhibit the broad teachings of the electrical circuits as potentially applied to a myriad of other architectures.

Note that in this Specification, references to various features (e.g., elements, structures, modules, components, steps, operations, characteristics, etc.) included in "one embodiment", "example embodiment", "an embodiment", "another embodiment", "some embodiments", "various embodiments", "other embodiments", "alternative embodiment", and the like are intended to mean that any such features are included in one or more embodiments of the present disclosure, but may or may not necessarily be combined in the same embodiments.

It is also important to note that the functions related to Farrow filters, illustrate only some of the possible filter functions that may be executed by, or within, systems illustrated in the FIGURES. Some of these operations may be deleted or removed where appropriate, or these operations may be modified or changed considerably without departing from the scope of the present disclosure. In addition, the timing of these operations may be altered considerably. The preceding operational flows have been offered for purposes of example and discussion. Substantial flexibility is provided by embodiments described herein in that any suitable arrangements, chronologies, configurations, and timing mechanisms may be provided without departing from the teachings of the present disclosure.

Numerous other changes, substitutions, variations, alterations, and modifications may be ascertained to one skilled in the art and it is intended that the present disclosure encompass all such changes, substitutions, variations, alterations, and modifications as falling within the scope of the appended claims. In order to assist the United States Patent and Trademark Office (USPTO) and, additionally, any readers of any patent issued on this application in interpreting the claims appended hereto, Applicant wishes to note that the Applicant: (a) does not intend any of the appended claims to invoke paragraph six (6) of 35 U.S.C. section 112 as it exists on the date of the filing hereof unless the words "means for" or "step for" are specifically used in the particular claims; and (b) does not intend, by any statement in the specification, to limit this disclosure in any way that is not otherwise reflected in the appended claims.

Other Notes, Examples, and Implementations

Note that all optional features of the apparatus described above may also be implemented with respect to the method or process described herein and specifics in the examples may be used anywhere in one or more embodiments.

In a first example, a system is provided (that can include any suitable circuitry, dividers, capacitors, resistors, inductors, ADCs, DFFs, logic gates, software, hardware, links, etc.) that can be part of any type of computer, which can further include a circuit board coupled to a plurality of electronic components. The system can include means for clocking data from the digital core onto a first data output of a macro using a first clock, the first clock being a macro clock; means for clocking the data from the first data output of the macro into the physical interface using a second clock, the second clock being a physical interface clock; means for clocking a first reset signal from the digital core onto a reset output of the macro using the macro clock, the first reset signal output used as a second reset signal; means for sampling the second reset signal using a third clock, which provides a clock rate greater than the rate of the second clock, to generate a sampled reset signal; and means for resetting the second clock to a predetermined state in the physical interface in response to a transition of the sampled reset signal.

The 'means for' in these instances (above) can include (but is not limited to) using any suitable component discussed herein, along with any suitable software, circuitry, hub, computer code, logic, algorithms, hardware, controller, interface, link, bus, communication pathway, etc. In a second example, the system includes memory that further comprises machine-readable instructions that when executed cause the system to perform any of the activities discussed above.

What is claimed is:

1. An analog beamformer for ultrasound beamforming, comprising:
   an array of transducers for transmitting analog signals and receiving reflected analog signals and providing analog output signals;
   an array of analog filters configured to receive the analog output signals, sample the analog output signals to form sampled analog output signals, filter the sampled analog output signals, and output filtered sampled analog output signals; and
   a delay line for receiving the filtered sampled analog output signals from the array of analog filters and adding a delay to each of the filtered sampled analog output signals.

2. The analog beamformer of claim 1, wherein the received reflected analog signals are pressure waves, and wherein the array of transducers converts the received reflected analog signals to voltages.

3. The analog beamformer of claim 1, wherein the received reflected analog signals are pressure waves, and wherein the array of transducers converts the received reflected analog signals to currents.

4. The analog beamformer of claim 1, further comprising a farrow filter in the array of analog filters for filtering the sampled analog output signals.

5. The analog beamformer of claim 1, further comprising a fractional delay filter bank in the array of analog filters for filtering the sampled analog output signals.

6. The analog beamformer of claim 5, wherein the fractional delay filter bank uses skewed sampling to select a subsample for transmitting with the filtered sampled analog output signals.

7. The analog beamformer of claim 5, further comprising a digital skew generator in the fractional delay filter bank for generating a time skew of delay between channels.

8. The analog beamformer of claim 1, further comprising a finite impulse response filter in the array of analog filters for filtering the sampled analog output signals.

9. The analog beamformer of claim 1, further comprising a summation module for summing the filtered sampled analog output signals and generating a beamformer output.

10. The analog beamformer of claim 1, further comprising an apodization circuit for windowing of a waveform of the transmitted analog signals to reduce sidelobes.

11. A analog beamformer for ultrasound beamforming, comprising:
    an array of analog filters for sampling and filtering analog signals to form sampled analog signals, adding a delay to the sampled analog signals to form delayed sampled analog signals, beamforming the delayed sampled analog signals, and outputting an output analog beamformed signal; and
    a summation node configured to receive the output analog beamformed signal and to receive at least a second output analog beamformed signal, and further configured to add the output analog beamformed signal to the second output analog beamformed signal.

12. The analog beamformer of claim 11, further comprising a farrow filter in the array of analog filters for introducing the delay to the sampled analog signals.

13. The analog beamformer of claim 11, further comprising a fractional delay filter bank in the array of analog filters for filtering the analog signals to form the sampled analog signals.

14. The analog beamformer of claim 13, wherein the fractional delay filter bank uses skewed sampling to select a subsample for transmitting with the sampled analog signals.

15. The analog beamformer of claim 13, further comprising a digital skew generator in the fractional delay filter bank for generating a time skew of delay between channels.

16. The analog beamformer of claim 11, further comprising a finite impulse response filter in the array of analog filters for filtering the sampled analog signals.

17. The analog beamformer of claim 11, further comprising an apodization circuit for windowing of a waveform of the sampled analog signals to reduce sidelobes.

18. A method for analog beamforming, comprising:
    transmitting, from an array of transducers, analog signals;
    receiving, at the array of transducers, reflected analog signals;
    filtering the received reflected analog signals with an array of analog filters, wherein filtering includes:
       sampling the received analog signals to generate sampled analog signals, and
       adding a delay to each of the sampled analog signals; and
    outputting, from the array of analog filters, a sampled analog output signal.

19. The method of claim 18, further comprising adding, at a summation node, the sampled analog ultrasound signal to parallel sampled analog output signals from parallel analog beamformers.

20. The method of claim 18, further comprising windowing, at an apodization circuit, a waveform of the sampled analog signals to reduce sidelobes.

* * * * *